US011751889B2

(12) United States Patent
Sommers et al.

(10) Patent No.: US 11,751,889 B2
(45) Date of Patent: Sep. 12, 2023

(54) DEVICES AND SYSTEMS FOR NAIL-BASED BONE FIXATION

(71) Applicant: Acumed LLC, Hillsboro, OR (US)

(72) Inventors: Mark B. Sommers, Beaverton, OR (US); Scott F. Mastroianni, Forest Grove, OR (US); James G. Falkner, Jr., Beaverton, OR (US); Roy Sanders, Tampa, FL (US); Dustin Cluff, St. Helens, OR (US); Steven D. Crawford, Carlton, OR (US); Marcus Mohr, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 76 days.

(21) Appl. No.: 17/496,195

(22) Filed: Oct. 7, 2021

(65) Prior Publication Data
US 2022/0110643 A1   Apr. 14, 2022

Related U.S. Application Data

(60) Provisional application No. 63/089,337, filed on Oct. 8, 2020.

(51) Int. Cl.
*A61B 17/17*   (2006.01)
*A61B 90/00*   (2016.01)
*A61B 17/00*   (2006.01)

(52) U.S. Cl.
CPC .......... *A61B 17/1717* (2013.01); *A61B 90/06* (2016.02); *A61B 90/08* (2016.02);
(Continued)

(58) Field of Classification Search
CPC . A61B 17/28; A61B 17/2804; A61B 17/2812; A61B 17/2816; A61B 17/282;
(Continued)

(56) References Cited

U.S. PATENT DOCUMENTS 7,785,326 B2   8/2010 Green et al.
10,758,280 B2   9/2020 Sommers et al.
(Continued)

OTHER PUBLICATIONS

International Search Report corresponding to related International Patent Application No. PCT/US2021/053905 dated Feb. 15, 2022, 5 pages.
(Continued)

Primary Examiner — Samuel S Hanna
(74) Attorney, Agent, or Firm — K&L Gates LLP

(57) ABSTRACT

The present disclosure provides a clamp composed of four distinct components. The ability to deconstruct the provided clamp into four components as compared to a typical two-part clamp may allow for greater ease in cleaning and sterilization. The provided clamp may include a first arm, a second arm, a cannula block, and a rotary cannula. In some instances, the provided clamp may include a locking feature for locking the rotary cannula to, and releasing it from, the cannula block. The present disclosure also provides a clamp including a scale for bone size determination, a clamp including a scale for determining how much compression force is being applied to a bone between the clamp's jaws, a system including a bushing and a set screw in which the set screw is self-locking, and a drill component system for preparing an opening in bone for a fixation component.

17 Claims, 17 Drawing Sheets

(52) U.S. Cl.
CPC .............. *A61B 2017/00407* (2013.01); *A61B 2090/064* (2016.02); *A61B 2090/0807* (2016.02)

(58) Field of Classification Search
CPC ........ A61B 17/2833; A61B 2017/2837; A61B 17/2841; A61B 2017/2825; A61B 17/1615; A61B 17/1617; A61B 17/17; A61B 17/1714; A61B 17/171; A61B 17/1717; A61B 17/1721; A61B 17/1725; A61B 17/1728; A61B 17/1732; A61B 17/1735; A61B 17/1739
See application file for complete search history.

(56) References Cited

U.S. PATENT DOCUMENTS

| | | |
|---|---|---|
| 2008/0183179 A1 | 7/2008 | Siebel et al. |
| 2012/0197291 A1 | 8/2012 | Tsai et al. |
| 2014/0329200 A1 | 11/2014 | Mahl |
| 2017/0181757 A1 | 6/2017 | Viola et al. |
| 2019/0105087 A1* | 4/2019 | Sommers ........... A61B 17/7233 |

OTHER PUBLICATIONS

International Written Opinion corresponding to related International Patent Application No. PCT/US2021/053905 dated Feb. 15, 2022, 8 pages.

International Preliminary Report corresponding to related International Patent Application No. PCT/US2021/053905 dated Apr. 20, 2023, 10 pages.

\* cited by examiner

DEVICES AND SYSTEMS FOR NAIL-BASED BONE FIXATION

PRIORITY CLAIM

The present application claims priority to and the benefit of U.S. Provisional Application 63/089,337, filed Oct. 8, 2020, the entirety of which is herein incorporated by reference.

BACKGROUND

An intramedullary (IM) nail is an internal fixation device that can be placed along the medullary canal of a fractured bone. The nail acts as a splint inside the bone to keep segments of the bone aligned as healing occurs. A standard, double-locking nail defines a plurality of apertures near its opposite ends to receive screws that lock both ends of the nail to bone. However, some bones, such as the fibula and ulna, can be too narrow to receive a standard nail without excessive reaming. For these bones, a slender, single-locking nail may be installed instead. The single-locking nail has a head defining apertures for screws, and a stem that is too thin to receive screws. Accordingly, one end of the nail (the head) is locked to the bone, but the other end (the stem) remains unlocked. If the bone is fractured at a position spanned by the stem, the nail may permit movement of bone segments relative to one another. For this type of fracture, the bone could be stabilized more effectively if the surgeon had the option of also locking the stem to the bone.

U.S. Pat. No. 7,785,326 proposes a nail-based fixation system in which a nail extends through, and is locked to, a fastener. More particularly, the system utilizes an installation jig that requires the nail to travel a linear path during advancement into bone, until the leading end of the nail has entered a hole of the fastener. However, this system is unsuitable for locking the stem of a nonlinear and/or flexible nail to bone at a substantial distance from the site of entry of the nail into the bone.

U.S. Pat. No. 10,758,280 provides a nail-based fixation system that aims to solve this drawback among others in typical nail-based fixation systems. The present disclosure aims to improve upon various aspects of the nail-based fixation system provided in U.S. Pat. No. 10,758,280.

SUMMARY

The present disclosure provides new and innovative systems and methods for nail-based bone fixation. In one aspect, the present disclosure provides a clamp composed of four distinct components. The ability to deconstruct the provided clamp into four components as compared to a typical two-part clamp may allow for greater ease in cleaning and sterilization. The provided four-part clamp enables a surgeon or other medical professional to utilize only the cannula block in certain instances. The four-part clamp may include two separate arms, a cannula block, and a rotary cannula. In some instances, the provided clamp may include a locking feature for locking the rotary cannula to, and releasing it from, the cannula block.

In another aspect, the present disclosure provides a clamp including a scale for bone size determination. In another aspect, the present disclosure provides a clamp including a scale for determining how much compression force is being applied to a bone between the clamp's jaws. In another aspect, the present disclosure provides a system including a bushing and a set screw. The bushing and set screw may lock a nail to the bushing as part of a nail-based bone fixation system. In another aspect, the present disclosure provides a drill component system for preparing an opening in bone for a fixation component, such as a screw or bushing (e.g., the presently disclosed bushing).

DETAILED DESCRIPTION

Figure 1:
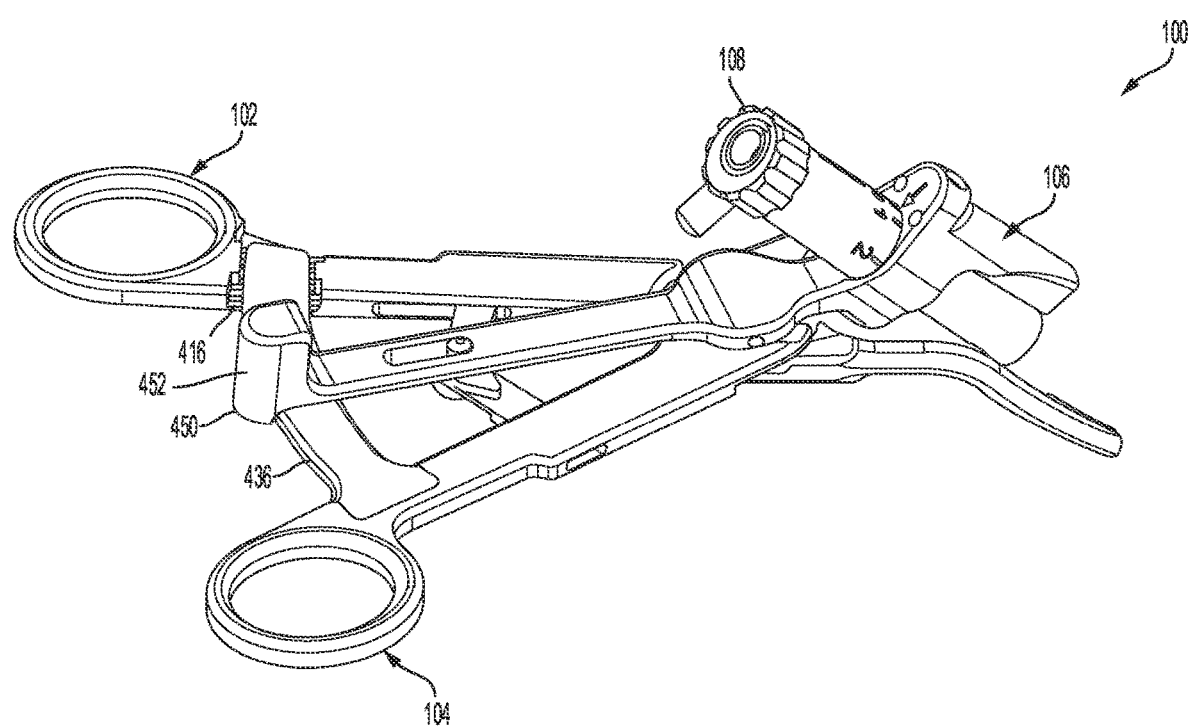
FIG. 1 illustrates a perspective view of a clamp, according to an aspect of the present disclosure.

The present disclosure provides devices and systems for nail-based bone fixation. In at least some aspects, the provided devices and systems aim to improve upon various aspects of the devices and systems disclosed in U.S. Pat. No. 10,758,280 ("the '280 devices and systems"). For instance, in various aspects, the provided devices and systems aim to improve the accuracy, reliability, and/or user experience of utilizing the '280 devices and systems to lock the tip of a nail, which helps increase fracture stability.

In one aspect, the present disclosure provides a clamp composed of four distinct components. The ability to deconstruct the provided clamp into four components as compared to a typical two-part clamp may allow for greater ease in cleaning and sterilization. For example, it may be easier to penetrate every portion of each of the clamp's components and interfaces with cleaning or sterilizing media as compared to a two-part clamp that may include connection points which are difficult to reach with cleaning or sterilizing product. In at least some aspects, the provided clamp includes a first arm, a second arm, a cannula block, and a rotary cannula. In various instances, the first and second arms are configured to lock the cannula block to the first and second arms. In some instances, a ratchet connection including a ratchet member and a ratchet receiver may connect the first and second arms. The first arm may include the ratchet member and the second arm includes the ratchet receiver, or vice versa. In other instances, another suitable connection may connect the first and second arms. The cannula block includes an opening through which the rotary cannula may be positioned.

In some aspects, the cannula block may include one or more holes for one or more fixation instruments. For example, the cannula block holes may be sized for k-wires to be translated through. In such aspects, the provided four-part clamp enables a surgeon or other medical professional to utilize only the cannula block in certain instances. For example, in some instances, a surgeon may desire to limit an incision size in a procedure. Inserting the clamp's jaws would require a greater incision than inserting solely the cannula block, and therefore the surgeon may desire the option to utilize only the cannula block. The cannula block, in such instances, may be secured to bone via one or more fixation instrument (e.g., k-wires) positioned through the cannula block's one or more holes.

In some instances, the provided clamp may include a locking feature for locking the rotary cannula to, and releasing it from, the cannula block. The locking feature may include a groove in the rotary cannula and a tab on the cannula block. In such instances, the rotary cannula's groove may terminate at a flat portion on the rotary cannula. The rotary cannula may be inserted into the cannula block's opening with the rotary cannula's flat portion oriented such that the cannula block's tab slides along the flat portion until the tab is lined up with the groove. The rotary cannula may then be rotated so that the tab enters the groove. When the tab is within the groove, the rotary cannula is locked to the cannula block with respect to an axial direction of the rotary cannula.

In another aspect, the present disclosure provides a clamp including a scale for bone size determination. The scale for bone size determination may be included on the provided four-part clamp or may be provided on any other suitable clamp. For example, a surgeon or other medical professional may clamp down on a bone with each of the provided clamp's jaws and take a reading from the bone size scale to determine a size of the bone between the jaws. Knowledge of the bone size can be helpful for a surgeon or other medical professional to select a size of an implant (e.g., screw, bushing, rod, nail, arthroplasty, etc.) or to determine if a bone may be too small for a particular surgical procedure. In some aspects, the bone size scale may be on the ratchet member of one of the arms. The opposing arm with the ratchet receiver, in some instances, may include an indicator that lines up with a section of the scale to indicate a measurement.

In another aspect, the present disclosure provides a clamp including a scale for determining how much compression force is being applied to a bone between the clamp's jaws. The scale for compression force determination may be included on the provided four-part clamp or may be provided on any other suitable clamp. In some instances, a first or second arm of the provided clamp having a compression force scale may include an indicator arm that lines us with a section of the compression force scale to indicate a measurement.

In another aspect, the present disclosure provides a system including a bushing and a set screw. The bushing and set screw may lock a nail to the bushing as part of a nail-based bone fixation system. The set screw may be inserted into the bushing and presses the nail against the bushing to lock the nail to the bushing. In combination with the construction of the bushing's internal threads, the set screw may be self-locking to the bushing, which helps prevent the set screw from loosening in order to maintain a desired position of the bushing relative to the nail. In some instances, the set screw may include a non-threaded leading end. In some instances, the set screw may include a tapered leading end. The non-threaded and/or tapered leading end may help guide the set screw into the bushing's internal threads to help prevent cross-threading and/or oblique initial insertion. In various aspects, the bushing may include a threaded body portion and a nipple extending from the threaded body portion. In at least one aspect, when the bushing is utilized in a bone fixation procedure, the threaded body portion engages the near cortex and the nipple engages the far cortex.

In another aspect, the present disclosure provides a drill component system for preparing an opening in bone for a fixation component, such as a screw or bushing (e.g., the presently disclosed bushing). The drill component system helps ensure that a surgeon or other medical professional does not accidentally over-drill either the near cortex or the far cortex. Such over-drilling would reduce the fixation component's engagement with the bone and would therefore reduce its holding power dramatically. In various instances, the drill component system may include a near cortex drill component and a far cortex drill component. In at least some aspects, a surgeon or other medical professional may position the near cortex drill component or far cortex drill component through a cannula (e.g., the provided clamp's rotary cannula) to drill into bone.

In at least some aspects, the near cortex drill component includes a shaft having a shoulder. The shoulder is sized such that it cannot fit through the cannula and therefore limits the depth to which the near cortex drill component can drill. The shoulder is positioned on the shaft such that drilling advancement of the near cortex drill component is prevented from reaching and drilling into the far cortex. After the near cortex drill component prepares a hole in the bone, the far cortex drill component may be advanced through the prepared hole. In at least some aspects, the far cortex drill component includes a shaft having a blunt reamer portion and a sharp trocar tip that extends from the blunt reamer portion. In at least some aspects, the shaft has a larger diameter than the sharp trocar tip. The sharp trocar tip may generate a hole in or through the far cortex.

The blunt reamer portion is constructed such that it does not penetrate the far cortex and therefore both prevents the far cortex drill component's shaft from penetrating the far cortex and limits the depth to which the sharp trocar tip may advance into the far cortex. For instance, the sharp trocar tip has a definite length and can advance no further than the definite length. In an example, the sharp trocar tip is constructed such that the hole it generates in the far cortex corresponds to the provided bushing's nipple, which creates a conforming fit for the provided bushing's nipple so that it maintains its position or fixation in the bone once installed. In this example, the blunt reamer portion is constructed such that it contours the inside of the bone canal to match the shape of the provided bushing's body portion.

In various instances, a system of the present disclosure may include one or more of the provided clamp, bushing, set screw, near cortex drill component, and far cortex drill component. For example, a system may include all of these components. In another example, a system may include the provided bushing, set screw, near cortex drill component, and far cortex drill component. In another example, a system may include the provided clamp, near cortex drill component, and far cortex drill component. Additional advantages of the present disclosure will be apparent from the following description of the figures.

Figure 2:
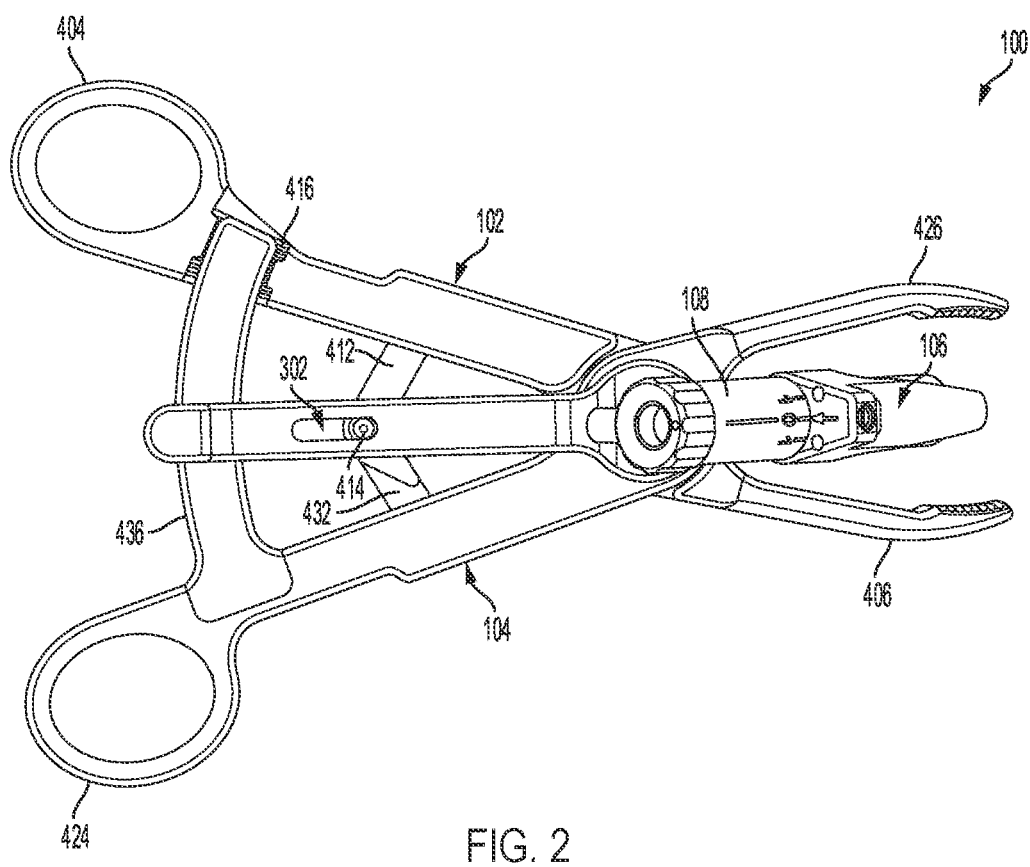
FIG. 2 illustrates a top view of the clamp of FIG. 1, according to an aspect of the present disclosure.
Figure 3:
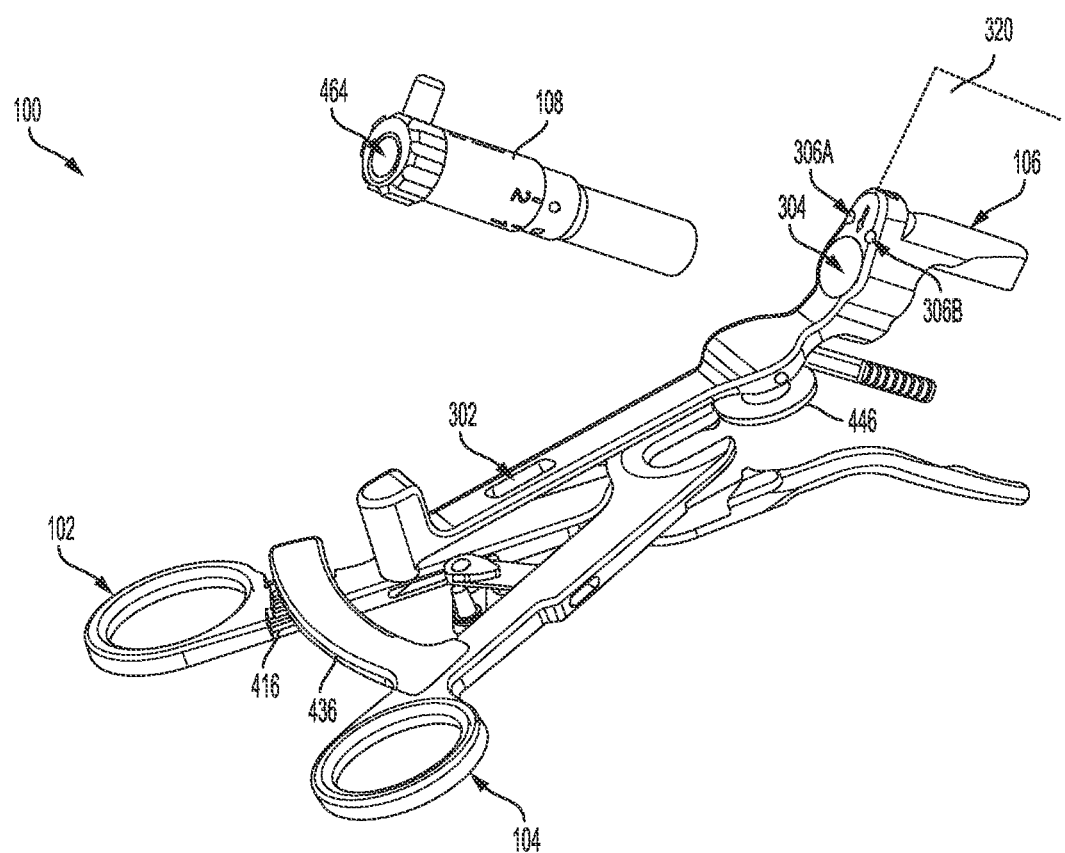
FIG. 3 illustrates an exploded view of the clamp of FIGS. 1 and 2, according to an aspect of the present disclosure.

FIGS. 1, 2, and 3, respectively illustrate a perspective view, top view, and exploded view of an example clamp 100. In at least some aspects, the clamp 100 includes a first arm 102, a second arm 104, a cannula block 106, and a rotary cannula 108. Each of the first arm 102, the second arm 104, the cannula block 106, and the rotary cannula 108 is its own separate and distinct component (e.g., see exploded view in FIG. 3). Stated differently, the clamp 100 may be deconstructed into four components—the first arm 102, the second arm 104, the cannula block 106, and the rotary cannula 108. The ability to deconstruct the clamp 100 into four components as compared to a typical two-part clamp may allow for greater ease in cleaning and sterilization of the components.

In various aspects, the first arm 102, the second arm 104, and the cannula block 106 rotate about a shared axis. The first arm 102 and the second arm 104 may rotate in a closing direction such that an arm 406 of the first arm 102 and an arm 426 of the second arm 104 move towards one another, or in an opening direction such that the arms 406 and 426 move away from one another. The construction of the clamp 100 that results in this shared rotation axis will be described more below in connection with FIGS. 5A and 5B. In various instances, the first arm 102 and the second arm 104 may respectively include a handle 404 and a handle 424. Surgeons or other medical professionals may place their fingers through the handles 404 and 424 to control the opening and closing of the arms 406 and 426.

In various aspects, the first arm 102, the second arm 104, and the cannula block 106 may interface to control a maximum closing between the arms 406 and 426 and a maximum opening between the arms 406 and 426. For example, the first arm 102 may include a branch 412 that includes a rod 414. The second arm 104 may include a branch 432 that includes an opening 434 (FIG. 4B). In other examples, the branches 412 and 432 may be reversed between the arms 102 and 104. The cannula block 106 may include an elongated opening 302. The opening 434 may be positioned over the rod 414 such that the branch 412 is connected to the branch 432. Connecting the branch 412 to the branch 432 may help maintain the first arm 102 and the second arm 104 in the assembled configuration. The elongated opening 302 may be positioned over the rod 414 on top of the branch 432. In this configuration, as the arms 102 and 104 move in the opening and closing directions, the rod 414 translates within the elongated opening 302. When the rod 414 contacts one of the ends of the elongated opening 302, the arms 102 and 104 are prevented from either opening or closing any further. Limiting the maximum closing and opening between the arms 406 and 426 of the arms 102 and 104, respectively, may help maintain the ratcheted connection between the arms 102 and 104.

In at least some aspects, the first arm 102 and the second arm 104 are connected such that a positioning of the first arm 102 and the second arm 104 is maintained in the absence of applied force. For example, the first arm 102 and the second arm 104 may be connected by a ratcheted connection that includes a ratchet member 436 and a ratchet receiver 416. In the illustrated examples, the first arm 102 includes the ratchet receiver 416 and the second arm 104 includes the ratchet member 436, though in other examples this may be reversed. The ratchet member 436 and/or the ratchet receiver 416, in various instances, may be connected to or integral with their respective arms 102 and 104. The ratchet member 436 and the ratchet receiver 416 may each include sets of teeth that engage one another. In various aspects, the engagement of the ratchet member 436 and the ratchet receiver 416 allow the first arm 102 and the second arm 104 to move in a closing direction (e.g., the jaw 406 moves towards the jaw 426), but not the opposite direction until the sets of teeth and a pawl are disengaged from one another. In other examples, the first arm 102 and the second arm 104 may be connected in suitable manners other than a ratcheted connection that enables maintaining a position of the first arm 102 and the second arm 104 in the absence of applied force (e.g., a speed lock connection).

In various aspects, the cannula block 106 includes a cannulation or channel 304. The rotary cannula 108 may be positioned partially through the channel 304. In at least some aspects, a long axis of the channel 304 may be offset from a long axis of a channel 464 of the rotary cannula 108, which is described in more detail with respect to FIGS. 7A and 7B. A plane 320 may extend through the long axis of the channel 304 of the cannula block 106. In at least some aspects, the cannula block 106 includes one or more channels 306A and 306B for one or more fixation instruments, such as k-wires. The k-wires may be advanced through the one or more channels 306A and 306B in order to fix the cannula block 106 to bone. In certain instances, the ability to deconstruct the clamp 100 such that the cannula block 106 is its own distinct component, and to fix the cannula block 106 to bone via one or more fixation instruments, enables a surgeon or other medical professional to use the cannula block 106 on its own without the other components of the clamp 100. For example, in some instances, a surgeon may desire to limit an incision size in a procedure. Inserting the jaws 406 and 426 of the clamp 100 would require a greater incision than inserting solely the cannula block 106, and therefore the surgeon may desire the option to utilize only the cannula block 106.

Figure 4A:
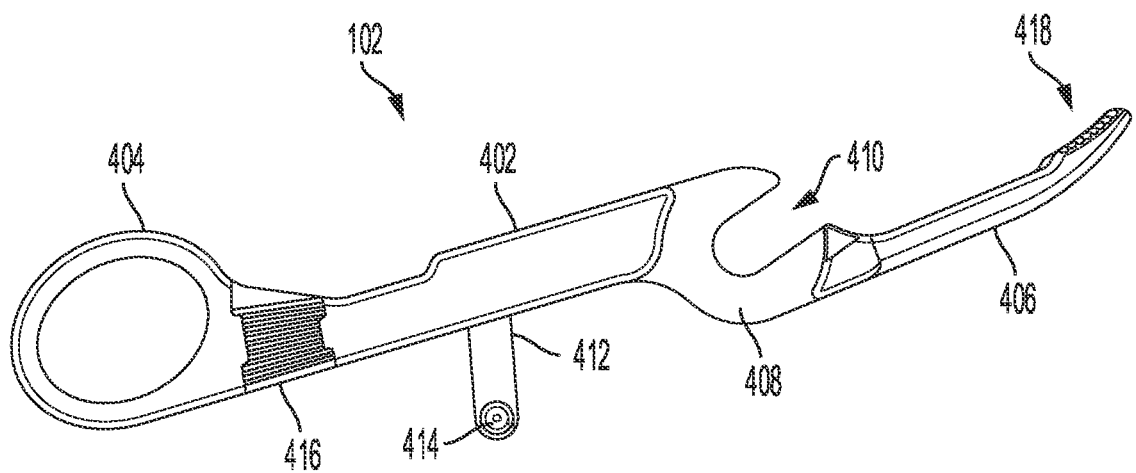
FIG. 4A illustrates a top view of an example first arm, according to an aspect of the present disclosure.
Figure 4B:
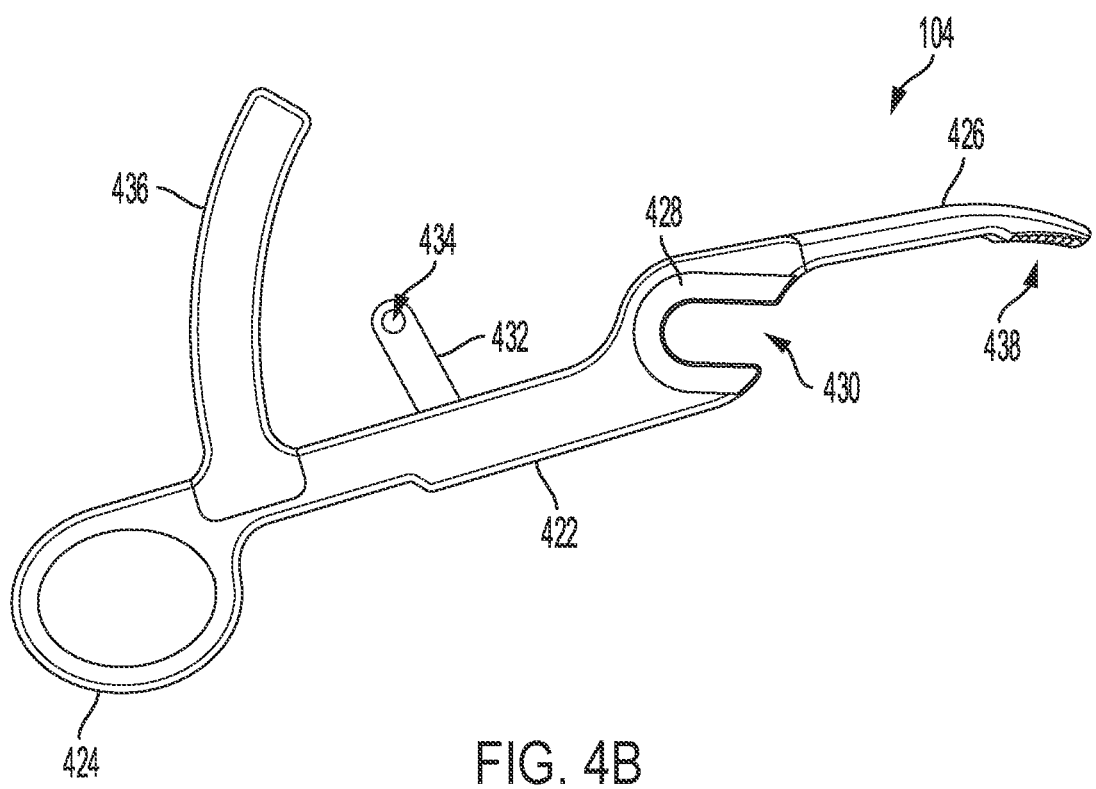
FIG. 4B illustrates a top view of an example second arm, according to an aspect of the present disclosure.

FIG. 4A illustrates a top view of an example first arm 102. The first arm 102 includes a body portion 402. At one end, the body portion 402 may include the handle 404 in various aspects. The handle 404 may have any suitable shape that enables surgeons or medical professionals to control the clamp 100 with their hands or fingers. At its opposing or clamping end, the body portion 402 may include the jaw 406. In various instances, the jaw 406 may include teeth 418. The teeth 418 may help increase traction of the jaw 406 on a bone so that the clamp 100 remains in position during a surgical procedure. In at least some aspects, the body portion 402 may include a recessed surface 408. The recessed surface 408 may be configured such that a portion of the second arm 104 may be positioned on the recessed surface 408 and the first and second arms 102 and 104 may rotate with respect to one another. In at least some aspects, the body portion 402 includes a slot 410.

As described above, in at least some aspects, a branch 412 may extend from the body portion 402. In some instances, the branch 412 may include the rod 414. In at least some aspects, the body portion 402 may include the ratchet receiver 416. In various instances, the ratchet receiver 416 may be connected to or integral with the body portion 402. The ratchet receiver 416 may include a set of teeth.

FIG. 4B illustrates a top view of an example second arm 104. The second arm 104 includes a body portion 422. At one end, the body portion 422 may include the handle 424 in various aspects. The handle 424 may have any suitable shape that enables surgeons or medical professionals to control the clamp 100 with their hands or fingers. At its opposing or clamping end, the body portion 422 may include the jaw 426. In various instances, the jaw 426 may include teeth 438. The teeth 438 may help increase traction of the jaw 426 on a bone so that the clamp 100 remains in position during a surgical procedure. In at least some aspects, the body portion 422 may include a recessed surface 428. The recessed surface 428 may be configured such that a portion of the cannula block 106 may be positioned on the recessed surface 428 and the arm 104 may rotate with respect to the cannula block 106. In at least some aspects, the body portion 422 includes a slot 430.

As described above, in at least some aspects, a branch 432 may extend from the body portion 422. In some instances, the branch 432 may include the opening 434. In at least some aspects, the body portion 422 may include the ratchet member 436. In various instances, the ratchet member 436 may be connected to or integral with the body portion 422. The ratchet member 436 may include a set of teeth 502 (FIGS. 5A and 5B) that are configured to engage with the set of teeth of the ratchet receiver 416.

Figure 4C:
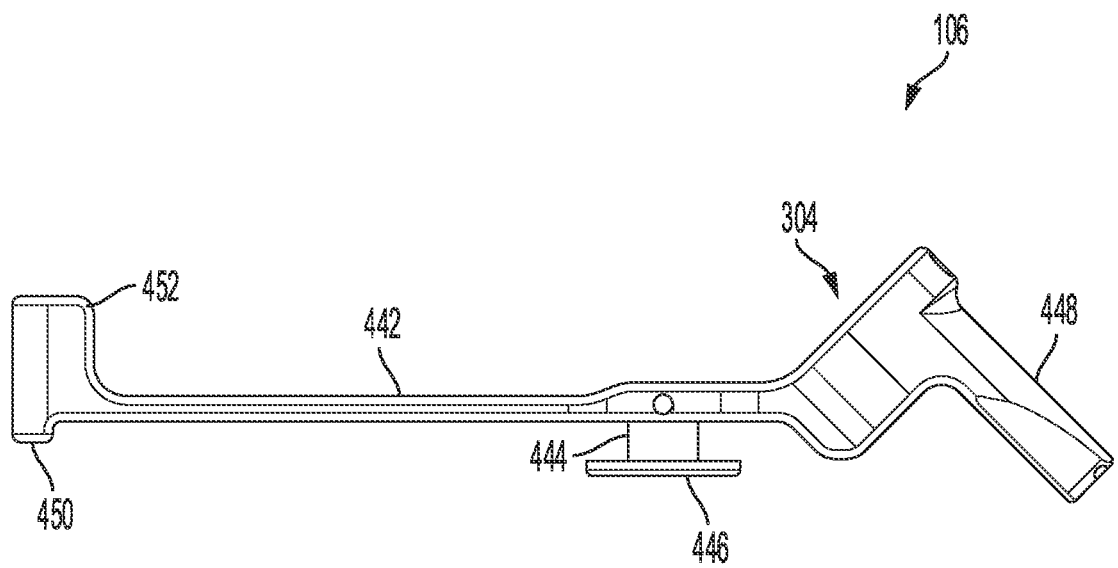
FIG. 4C illustrates a side view of an example cannula block, according to an aspect of the present disclosure.

FIG. 4C illustrates a side view of an example cannula block 106. The cannula block 106 includes a body portion 442. In some aspects, the body portion 442 may include an extension 450 at one of its ends. In some aspects, the body portion 442 may alternatively or additionally include a block 452 at the same end. The extension 450 may interface with the ratchet member 436 of the second arm 104 and help prevent the cannula block 106 from translating, which will be further explained in connection with FIGS. 5A and 5B. The block 452 may help a surgeon or other medical professional disassemble the clamp 100, as will also be explained in connection with FIGS. 5A and 5B.

In at least some aspects, the body portion 442 at its opposing end may include a support post 448. In various instances, the body portion 442 additionally or alternatively includes the channel 304 at the opposing end. The support post 448 may act as a support to maintain an alignment of the rotary cannula 108 when the rotary cannula 108 is positioned through the channel 304. In at least some aspects, a post 444 extends from the body portion 442. The post 444 may be configured such that it may be positioned within the slot 410 of the first arm 102 and the slot 430 of the second arm 104. The post 444 serves as a rotation axis of the clamp 100. In various examples, a cap 446 may be attached to or integral with the post 444.

Figure 4D:
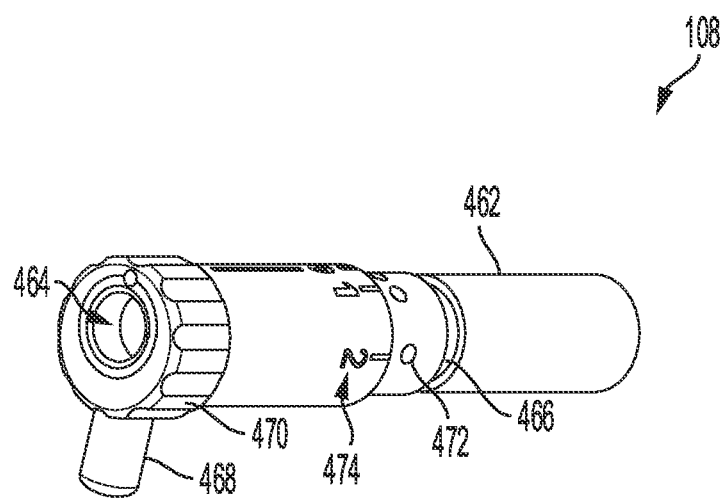
FIG. 4D illustrates a perspective view of an example rotary cannula, according to an aspect of the present disclosure.

FIG. 4D illustrates a perspective view of an example rotary cannula 108. The rotary cannula 108 includes a body portion 462. A cannula or channel 464 extends through a length of the body portion 462. In at least some aspects, the body portion 462 may include a groove 466. In various instances, the groove 466 may extend around a portion of the body portion 462 and terminate at a flat surface 708 (FIG. 7A) of the body portion 462, as will be described in more detail in connection with FIGS. 7A and 7B.

In some aspects, the body portion 462 may include a ridged surface 470 at one of its ends. The ridged surface 470 may increase an ease with which a surgeon or other medical professional may rotate the rotary cannula 108 as compared to a smooth surface. In some aspects, a handle 468 may extend from the body portion 462, such as from the ridged surface 470. The handle 468 may increase an ease with which a surgeon or other medical professional may rotate the rotary cannula 108. A position of the handle 468 with respect to the rest of the clamp 100 may indicate a position that the rotary cannula 108 is in (e.g., insert/removal position, operate position). In some examples, the body portion 462 may include a set of markings 474 that visually indicate a position that the rotary cannula 108 is in. In some aspects, the body portion 462 may include a plurality of detents 472. In such aspects, the plurality of detents 472 may interface with a ball plunger to provide arrested positions of the rotary cannula 108 at specific intervals.

Figure 5A:
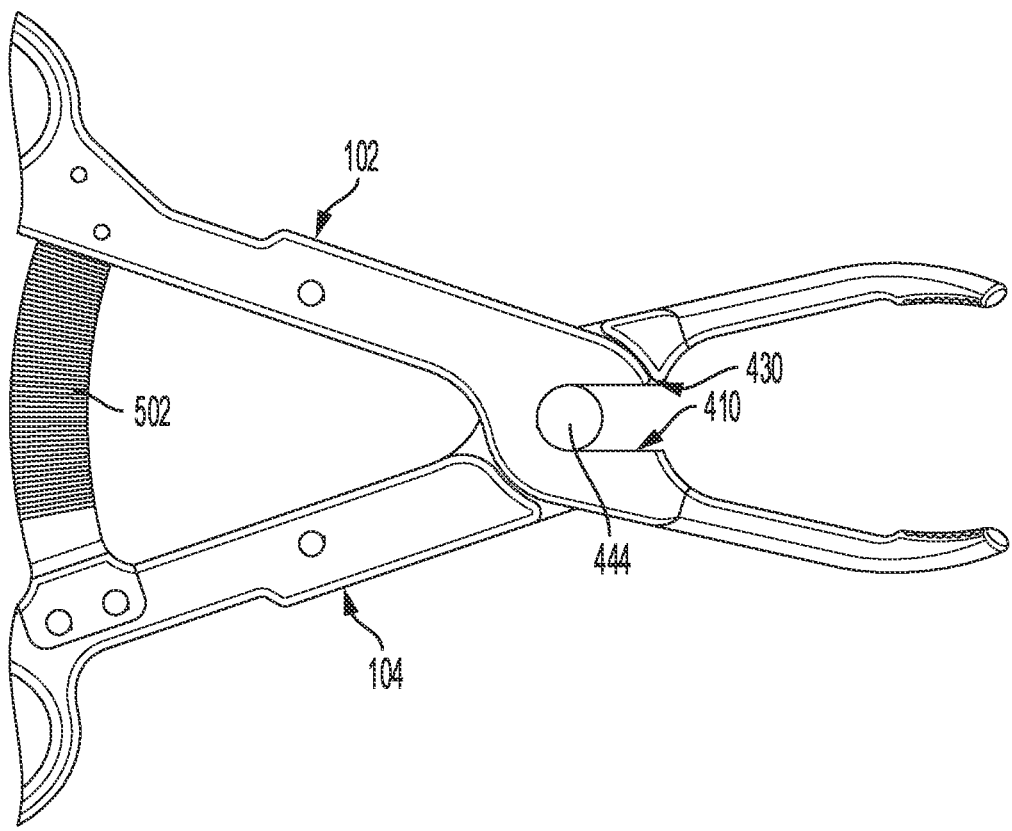
FIG. 5A illustrates a bottom view of an assemble/disassemble position of the first and second arms, according to an aspect of the present disclosure.
Figure 5B:
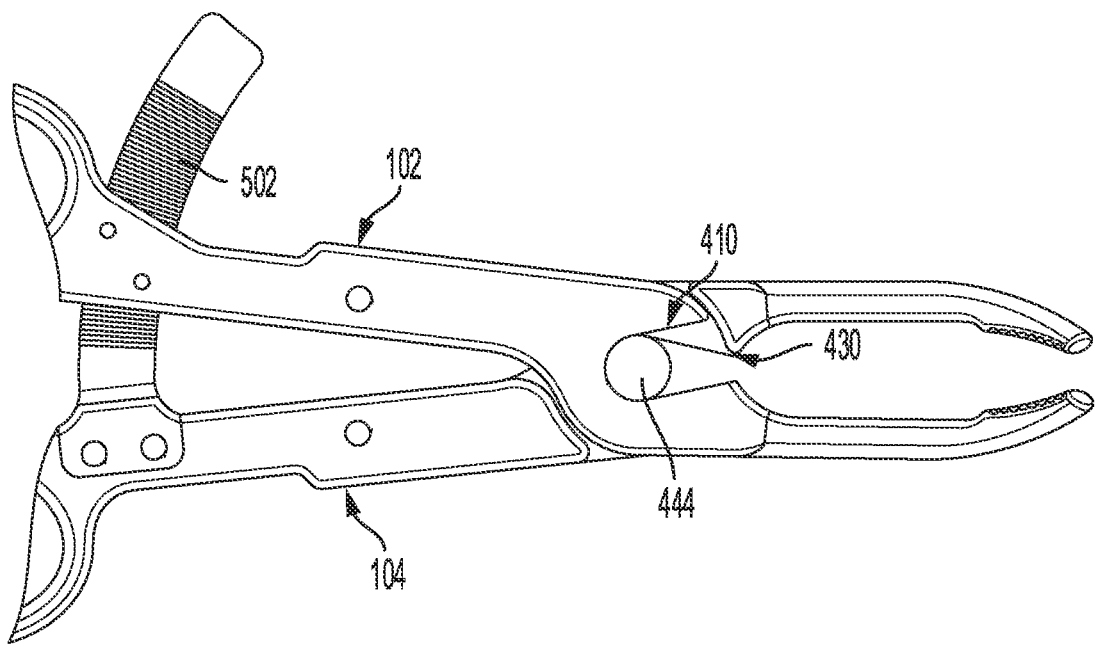
FIG. 5B illustrates a bottom view of an operate position of the first and second arms, according to an aspect of the present disclosure.

FIGS. 5A and 5B illustrate a bottom view of the coupling mechanism of the example clamp 100 that enables assembling the first arm 102, the second arm 104, and the cannula block 106. Only the first arm 102, the second arm 104, and the post 444 of the cannula block 106 are illustrated solely for the sake of clarity in the figures. FIG. 5A illustrates an assemble/disassemble position of the clamp 100. In the assemble/disassemble position, the slot 410 of the first arm 102 and the slot 430 of the second arm 104 are lined up with one another (e.g., parallel openings). In this position, the post 444 of the cannula block 106 is able to slide out of the slot 410 and the slot 430.

As described above, in some instances, the cannula block 106 may include an extension 450 that interfaces with the ratchet member 436. In such instances, the extension 450 may prevent the cannula block 106 from translating in a direction that enables the post 444 to exit the slots 410 and 430. By preventing this translation, the extension 450 may help prevent the cannula block 106 from disassembling out of the slots 410 and 430 when disassembly is not desired. For example, a surgeon or other medical professional may adjust the first arm 102 and the second arm 104 while using the clamp 100 during a surgical procedure such that the slots 410 and 430 match up, but at a time when the surgeon or other medical professional is using the clamp 100 and does not want it to disassemble. To disassemble the clamp 100, a surgeon or other medical professional may lift the extension 450 such that it no longer interfaces with the ratchet member 436 and then translate the cannula block 106 when the slots 410 and 430 are lined up to release the post 444 from the slots 410 and 430. For example, a surgeon or other medical professional may grab and lift the block 452, which lifts the extension 450, and translate the block 452 in order to release the cannula block 106 from the slots 410 and 430.

FIG. 5B illustrates an example operate position of the clamp 100. In the operate position, the first arm 102 and the second arm 104 are rotated relative to one another such that their respective slots 410 and 430 are not lined up (e.g., non-parallel openings). Because the slots 410 and 430 are not lined up (e.g., openings are not parallel), the post 444 is unable to translate out of the slots 410 and 430, but is rather prevented from doing so (e.g., trapped) by the respective body portions 402 and 422 of the first and second arms 102 and 104. Additionally, the connection between the branch 412 of the first arm 102 to the branch 432 of the second arm 104 may help maintain the first arm 102 and the second arm 104 in the assembled configuration by preventing the first arm 102 and the second arm 104 from sliding off the post 444. In at least some aspects, the cap 446 of the cannula block 106 prevents the first arm 102 and the second arm 104 from moving along an axial direction of the post 444 with respect to the cannula block 106. In such aspects, the post 444 may have a length equal to a thickness of the first arm 102 and the second arm 104 in order to minimize or eliminate axial movement.

In the operate position, the first arm 102, second arm 104, and cannula block 106 are coupled to one another while still enabling the first arm 102 and the second arm 104 to rotate partially around the post 444. The described coupling mechanism that enables assembly (and disassembly) of the clamp 100 enables the clamp 100 to provide a secure connection to the bone with the cannula block 106 being solidly connected to the first arm 102 and the second arm 104 in order to provide a stable and accurate position of rotary cannula 108. A stable and accurate position of the rotary cannula 108 helps a surgeon or other medical professional to drill accurate bone holes for a surgical procedure.

Figure 6:
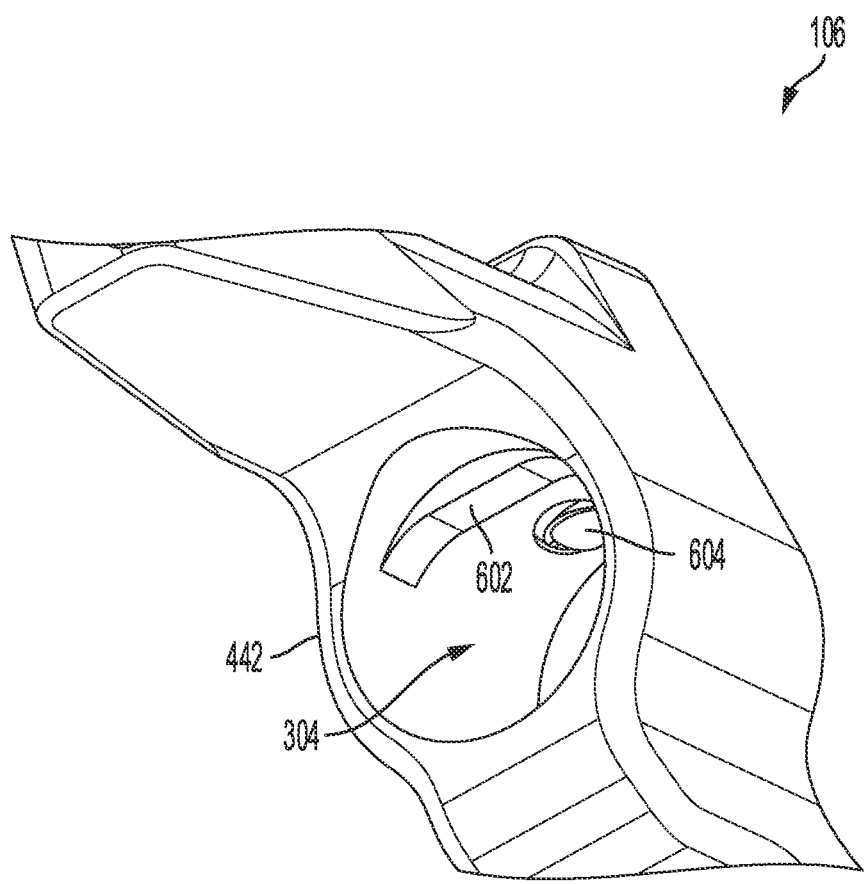
FIG. 6 illustrates a magnified perspective view of a channel of a cannula block, according to an aspect of the present disclosure.

FIG. 6 illustrates a magnified perspective view of the channel 304 of the cannula block 106. In at least some aspects, the body portion 442 of the cannula block 106 includes a tab 602 within the channel 304. The tab 602 extends into the channel 304 and may have any suitable shape. In at least some aspects, the cannula block 106 may include a ball plunger 604. In such aspects, the ball plunger 604 may, for example, be any suitable ball and spring plunger. The ball plunger 604 may extend into the channel 304 and may compress into the body portion 442 upon an applied force to the ball plunger 604.

Figure 7A:
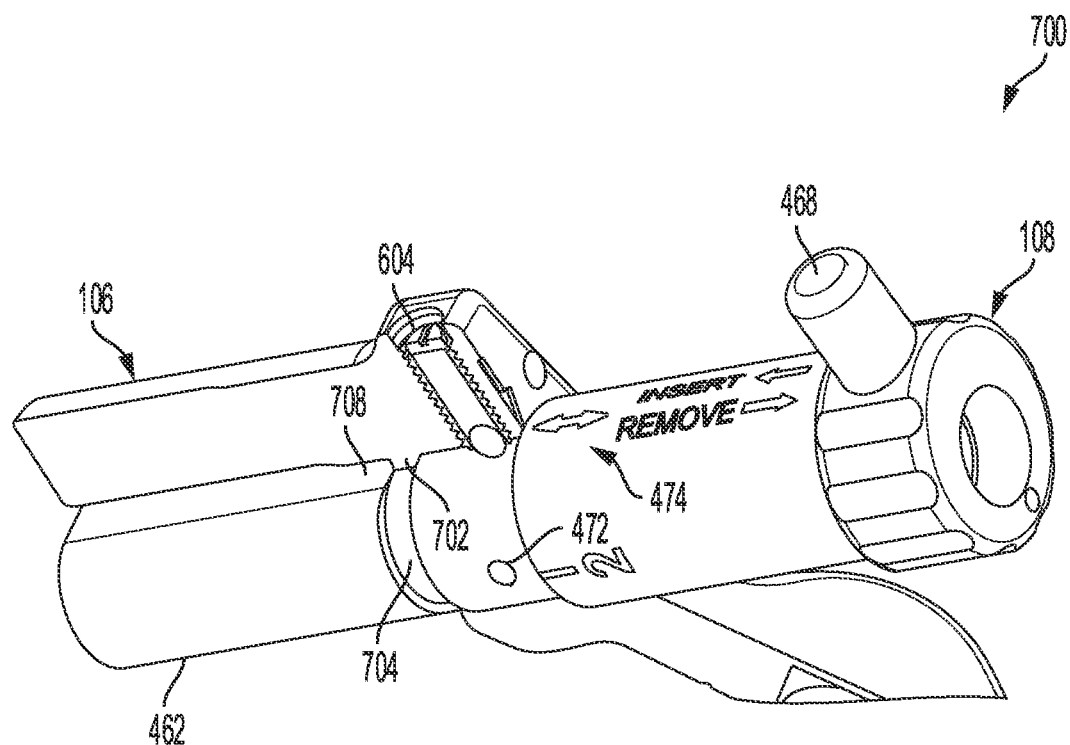
FIG. 7A illustrates a perspective view of an insert/remove position of the rotary cannula, according to an aspect of the present disclosure.
Figure 7B:
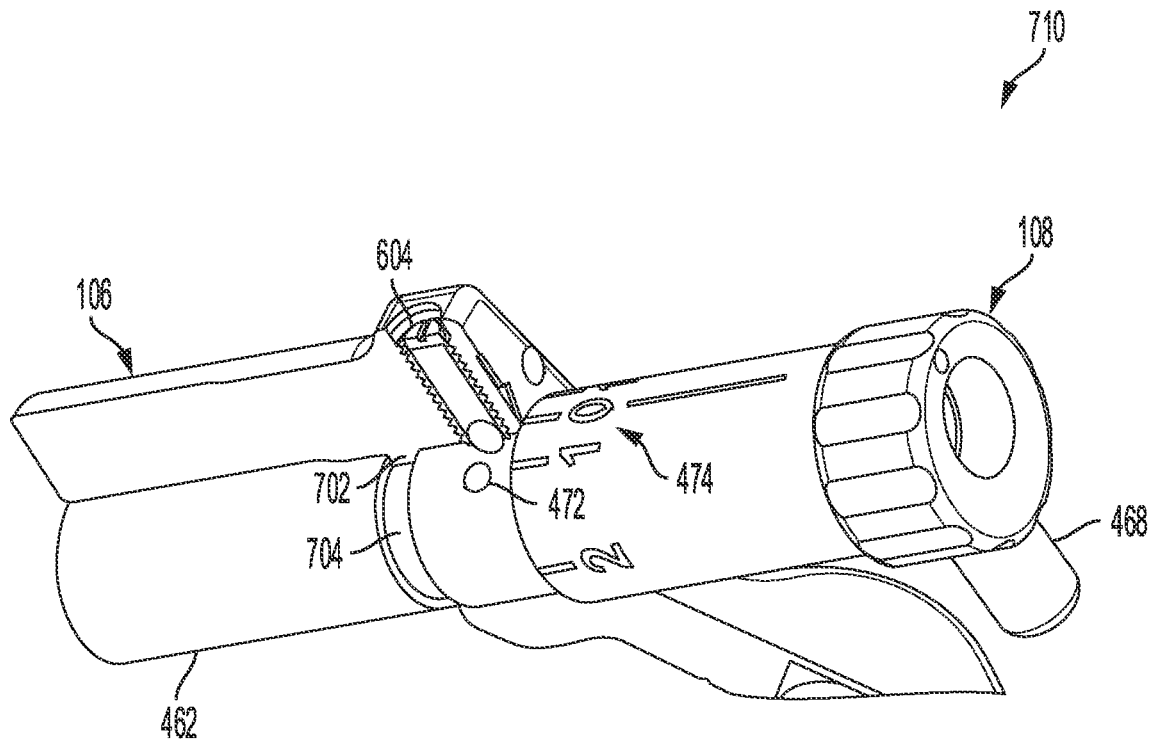
FIG. 7B illustrates a perspective view of a coupled position of the rotary cannula, according to an aspect of the present disclosure.

FIGS. 7A and 7B illustrate a locking feature of the example clamp 100 for coupling and releasing the rotary cannula 108 to and from the cannula block 106. The cannula block 106 is shown in cross section for illustrative purposes. The ability to decouple the rotary cannula 108 from the cannula block 106 allows for proper cleaning and sterilization of the rotary cannula 108 between surgeries. The ability to decouple the rotary cannula 108 from the cannula block 106 also helps reduce the storage footprint of the clamp 100 and enables easier storage in the surgical tray as compared to at least some typical clamps.

FIG. 7A illustrates an insert/remove position 700 of the rotary cannula 108. In the insert/remove position 700, a flat surface 708 of the body portion 462 of the rotary cannula 108 lines up with the tab 702 of the cannula block 106. The tab 702 may slide along the flat surface 708 such that the rotary cannula 108 can be inserted into and removed from the channel 304 of the cannula block 106. Stated differently, the tab 702 is not within the groove 704 in the insert/remove position 700. Rather, the groove 704 begins on opposing sides of the flat surface 708. As illustrated, the set of markings 474 of the rotary cannula 108 may indicate, in various aspects, that the rotary cannula 108 is in an insert/remove position 700. Additionally or alternatively, the direction of the handle 468 may indicate that the rotary cannula 108 is in the insert/remove position 700. In some instances, the ball plunger 604 may be positioned within a detent 472 when the rotary cannula 108 is in the insert/remove position 700.

FIG. 7B illustrates a coupled position 710 of the rotary cannula 108. In the coupled position 710, the tab 702 of the cannula block 106 is positioned within the groove 704 of the rotary cannula 108. The tab 702 prevents the rotary cannula 108 from translating into or out of the channel 304 of the cannula block 106. When the example clamp 100 is introduced at a surgical site, a surgeon or other medical professional pushes the clamp 100 through soft tissue onto a bone until the rotary cannula 108 sits flush with the near cortex of the bone (e.g., FIG. 14). The configuration of the tab 702 within the groove 704 enables the surgeon or other medical professional to apply axial force onto the rotary cannula 108 to push the rotary cannula 108 through the soft tissue without the rotary cannula 108 being pushed out of the cannula block 106. To transition to the coupled position 710 from the insert/remove position 700, a surgeon or other medical professional may rotate the rotary cannula 108. In one example, the coupled position 710 is a 180° rotation of the rotary cannula 108 from the insert/remove position 700.

In at least some aspects, a long axis of the channel 464 of the rotary cannula 108 is offset from a long axis of the channel 304 of the cannula block 106 when the rotary cannula 108 is positioned through the channel 304 of the cannula block 106. Stated differently, in some aspects, the channel 464 and the channel 304 are not coaxial when the rotary cannula 108 is positioned within the channel 304 of the cannula block 106. This offset configuration creates a cam effect that causes the channel 464 to translate relative to the plane 320 that extends through the long axis of the channel 304 when the rotary cannula 108 is rotated while positioned within the cannula block 106.

For example, the long axis of the channel 464 may initially be neutrally positioned such that the long axis of the channel 464 intersects the plane 320, and may similarly be neutrally positioned if the rotary cannula 108 is rotated a half revolution (180°). If the rotary cannula 108, however, is rotated less than a half revolution (e.g., greater than 0° but less than 180°) or more than a half revolution (e.g., greater than 180° but less than 360°), the long axis of the channel 464 translates away from the plane 320. A maximum translation of the long axis of the channel 464 away from the plane 320 may be achieved by rotating the rotary cannula 108 a quarter revolution from its starting position (90° or 270°). The amount of offset of the long axis of the channel 464 relative to the long axis of the channel 304 when the rotary cannula 108 is inserted through the channel 304 determines an amount that the long axis of the channel 464 translates relative to the plane 320 as the rotary cannula 108 is rotated. In an example, the offset may be two millimeters, which allows a maximum translation of two millimeters for the long axis of the rotary cannula 108 from the plane 320 that extends through the long axis of the channel 304.

In such aspects including this offset configuration, the clamp 100 may include multiple distinct coupled positions 710. For instance, the rotary cannula 108 may include multiple detents 472 with each representing a distinct coupled position 710 (aside from the detent 472 corresponding to the insert/remove position 700). When the ball plunger 604 is within a detent 472, the ball plunger 604 provides added resistance to rotate the rotary cannula 108 to help maintain a correct rotational position of the rotary cannula 108 until it is desired to change it. In an example, a detent 472 may be positioned such that the ball plunger 604 engages the detent 472 when the long axis of the rotary cannula 108 is oriented at a maximum translation (e.g., 2 mm) from the plane 320. In some instances, the rotary cannula 108 may include two separate detents 472 that each designate a maximum translation of the long axis of the rotary cannula 108. In some examples, the rotary cannula 108 may include one or more detents 472 that designate a translation (e.g., 1 mm) of the long axis of the rotary cannula 108 less than the maximum translation. As illustrated, the set of markings 474 may indicate, in various aspects, that the rotary cannula 108 is in a coupled position 710, and in some instances, which coupled position 710. Additionally or alternatively, the direction of the handle 468 may indicate that the rotary cannula 108 is in a coupled position 710, and in some instances, which particular coupled position 710.

In various aspects of the present disclosure, each of the components of the example clamp 100 may be constructed of a suitable medical grade material. For example, suitable medical grade materials may include carbon fiber reinforced PEEK, stainless steel, titanium, cobalt chromium, or other suitable plastics. In some instances, a suitable plastic includes the advantage of being radiolucent. In some instances, all of the components of the clamp 100 may be constructed of the same material. In other aspects, one or more of the components of the clamp 100 may be constructed of a material different than the other components. In at least some aspects, the first arm 102 and the second arm 104 may each be constructed of a material that is suitably rigid while also having elastic properties. For example, the first arm 102 and the second arm 104 may be constructed of titanium, carbon fiber reinforced plastic, stainless steel, or cobalt chromium.

Figure 8:
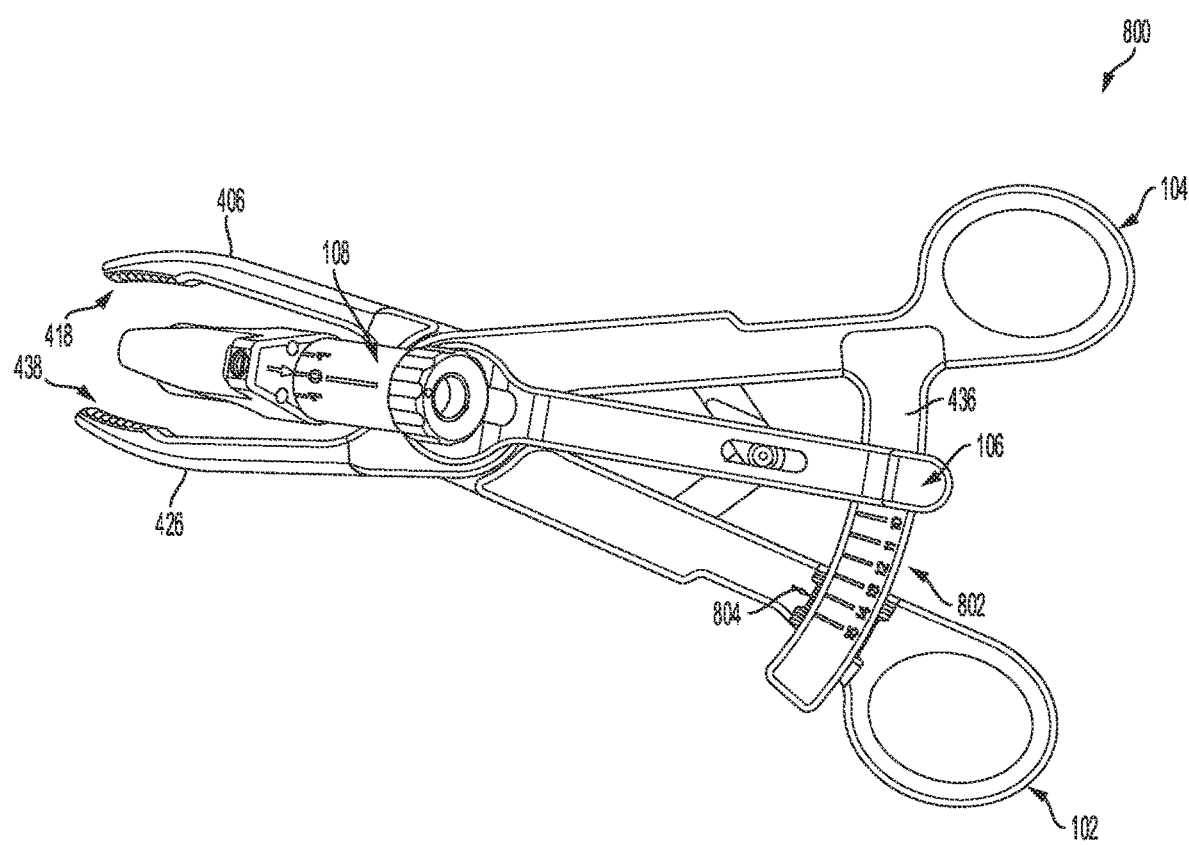
FIG. 8 illustrates perspective view of a clamp having a bone size scale for determining a size of a bone positioned between the clamp's first and second jaws, according to an aspect of the present disclosure.

The present disclosure additionally provides a new and innovative bone size scale for use with a surgical clamp. In some instances, it may be helpful for surgeons or other medical professionals to determine the size of the bone they are clamping on. Knowledge of the bone size (e.g., width between the teeth 418 of the first jaw 406 and the teeth 438 of the second jaw 426) can be useful for a surgeon or other medical professional to help select a size of an implant (e.g., screw, bushing, rod, nail, arthroplasty, etc.). Knowledge of the bone size can also be useful to determine if a bone is too small for a particular procedure. FIG. 8 illustrates an example clamp 800 having a bone size scale 802 for determining a size of a bone positioned between the first arm 102 and the second arm 104. In some instances, the bone size scale 802 may be included on the clamp 100, and therefore the components of the clamp 100 will be referred to in this description. In other instances, the provided bone size scale 802 may be included on any other suitable clamp.

In at least some aspects, the bone size scale 802 is positioned on the ratchet member 436. The bone size scale 802 may include a plurality of indicators (e.g., line markings, indentations, etc.) and/or values corresponding to particular bone sizes. In various instances, as the first arm 102 and the second arm 104 rotate relative to one another, a positioning of the ratchet member 436 relative to the first arm 102 changes, which changes a reading on the bone size scale 802. In other aspects, the clamp 800 may include a separate arm from the ratchet member 436 that includes the bone size scale 802. The separate arm may be connected to or integral with the second arm 104 (e.g., the same arm as the ratchet member 436). In some aspects, this separate arm may slide along the first arm 102 (e.g., the opposite arm of the one that the separate arm is connected to) as the first arm 102 and the second arm 104 rotate relative to one another.

Once the first arm 102 and the second arm 104 are in a desired position for a measurement (e.g., contacting a bone, but before clamping down), a surgeon or other medical professional may determine a bone size based on where a particular landmark (e.g., an edge of the first arm 102) lines up on the bone size scale 802. It may beneficial for the surgeon or other medical professional to determine the bone size while the first and second jaws 406 and 426 are contacting a bone, but prior to clamping down on the bone, because clamping down may deform the first arm 102 and the second arm 104 leading to a false bone size determination. In at least some examples, the first arm 102 may include an indicator 804, such as a line marking or indentation, as the particular landmark. In such examples, an indicator and/or value on the bone size scale 802 that lines up with the indicator 804 may be taken as a measured bone size.

Figure 9:
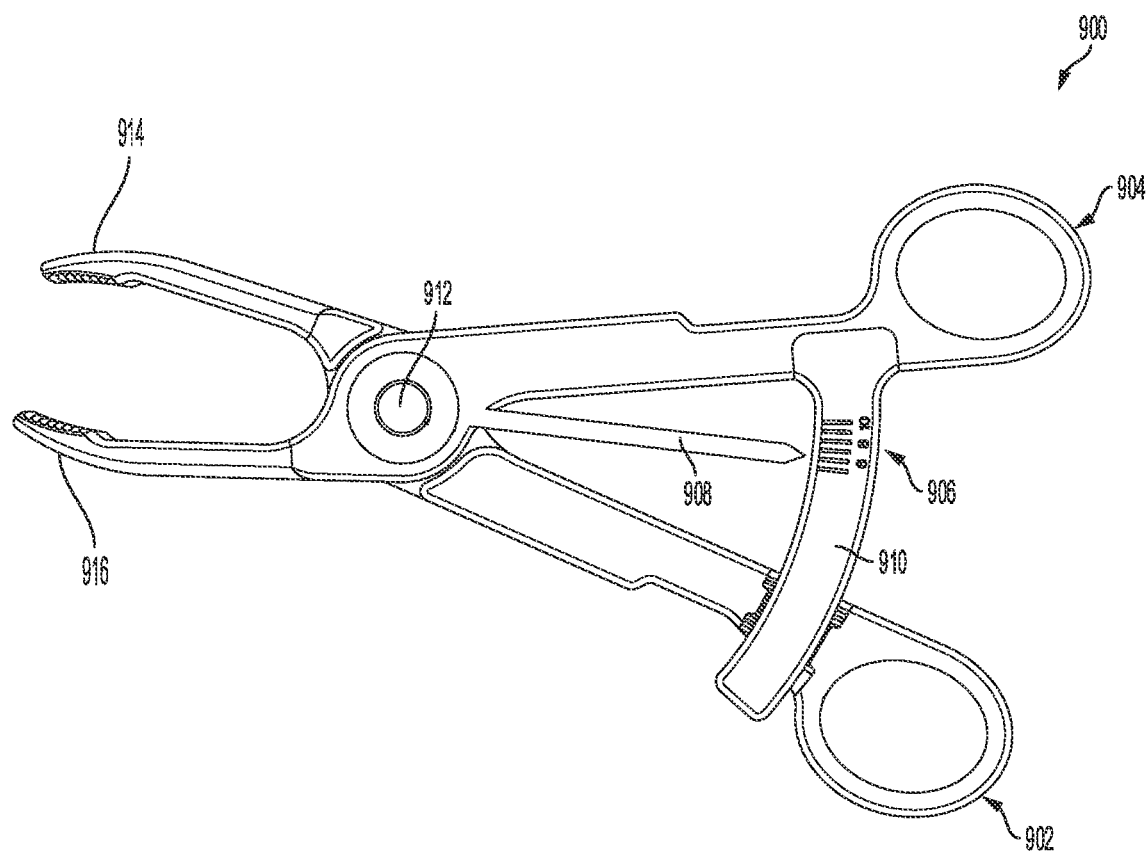
FIG. 9 illustrates perspective view of a clamp having a compression force scale for determining an amount of force being applied by the clamp's first and second jaws, according to an aspect of the present disclosure.

The present disclosure additionally provides a new and innovative compression force scale for use with a surgical clamp. In some instances, it may be helpful for surgeons or other medical professionals to determine how much force they are applying to a bone when clamping it. For example, it may be important for surgeons or other medical professionals to limit the amount of force they apply to osteoporotic bone so that they do not fracture the bone by clamping it. FIG. 9 illustrates an example clamp 900 having a compression force scale 906 for determining an amount of force being applied by a first jaw 914 of a first arm 902 and a second jaw 916 of a second arm 904. In some instances, the example clamp 900 may be similar to the clamp 100 with the added features of the compression force scale 906. In other instances, the clamp 900 may have the configuration of any other clamp suitable for implementing the compression force scale 906. For instance, in some examples, the first arm 902 may be coupled to the second arm 904 at a rotation joint 912.

In some aspects, the compression force scale 906 is positioned on a member 910 connected to or integral with the second arm 904. In some examples, the member 910 is a ratchet member. In other examples, the member 910 may be another suitable connecting member (e.g., a component of a speed lock connection) between the first arm 902 and the second arm 904. In some aspects, the compression force scale 906 may be positioned on a second member separate from the connecting member. The second, separate member may extend from the second arm 904 (e.g., the same arm as the connecting member). In some aspects, the separate arm may slide above or below the first jaw 902 (e.g., the opposite jaw of the one that the separate arm is connected to) as the first and second jaw 902 and 904 rotate relative to one another. In some instances, the compression force scale 906 may include a plurality of indicators (e.g., line markings, indentations, etc.) and/or values corresponding to particular amounts of force. In some instances, the compression force scale 906 may include a plurality of indicators (e.g., line markings, indentations, etc.) corresponding to a level or range of clamping force (e.g., high, medium, low).

In at least some aspects, the first arm 902 and the second arm 904 may be constructed of a material that has elastic properties. In such aspects, the first arm 902 and the second arm 904 may deform while being clamped onto a bone. The resulting deformation may cause an indicator arm 908 to move relative to the compression force scale 906. The elastic first and second arms 902 and 904 are calibrated to the compression force scale 906 based on the elastic properties and shape of the first and second arms 902 and 904. In at least some aspects, the indicator arm 908 may be connected to or integral with the second arm 904. Once the first arm 902 and the second arm 904 are in a desired position for a measurement (e.g., clamped on a bone), a surgeon or other medical professional may determine where the indicator arm 908 lines up on the compression force scale 906 to determine a compression force being applied to the bone between the first arm 902 and the second arm 904.

Figure 10:
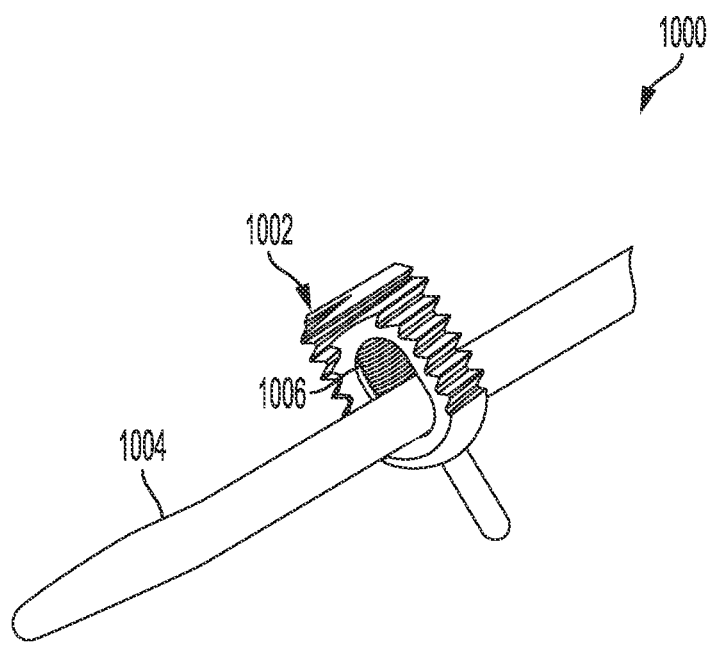
FIG. 10 illustrates a perspective view of a system including a bushing, a set screw, and a nail, according to an aspect of the present disclosure.
Figure 11:
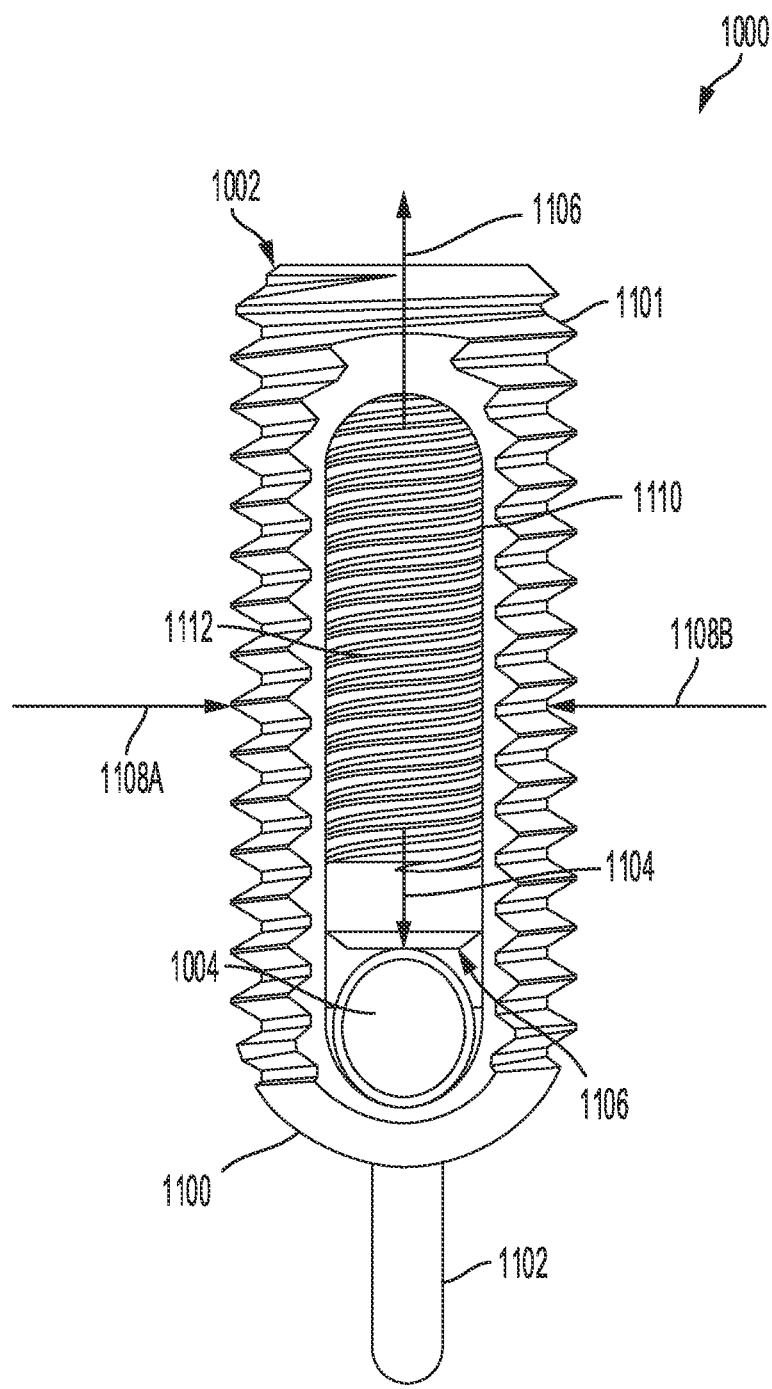
FIG. 11 illustrates a front view of the system of FIG. 10, according to an aspect of the present disclosure.

The present disclosure additionally provides a system including a bushing and a set screw. The provided bushing and set screw may lock a nail to the bushing as part of a nail-based bone fixation system. FIGS. 10 and 11 illustrate a perspective view and side view, respectively, of an example system 1000 including an example bushing 1002 and an example set screw 1006. In some instances, the example system 1000 may include a nail 1004. The set screw 1006 may be inserted into the bushing 1002 so that it presses the nail 1004 against the bushing 1002 (e.g., against an internal surface of the bushing as illustrated) to lock the nail 1004 to the bushing 1002. The nail 1004 is illustrated locked to the bushing 1002 by the set screw 1006.

In at least some aspects, the bushing 1002 includes a plurality of exterior threads 1101 on a body portion 1100. The body portion 1100 may include an opening 1110 that extends through the body portion 1100. In at least some aspects, the bushing 1002 includes a nipple 1102 that extends from the body portion 1100. In some examples, the nipple 1102 may be dull or smooth. In other examples, the nipple 1102 may include a sharp end. In some examples, the nipple 1102 may include external threads.

Figure 12:
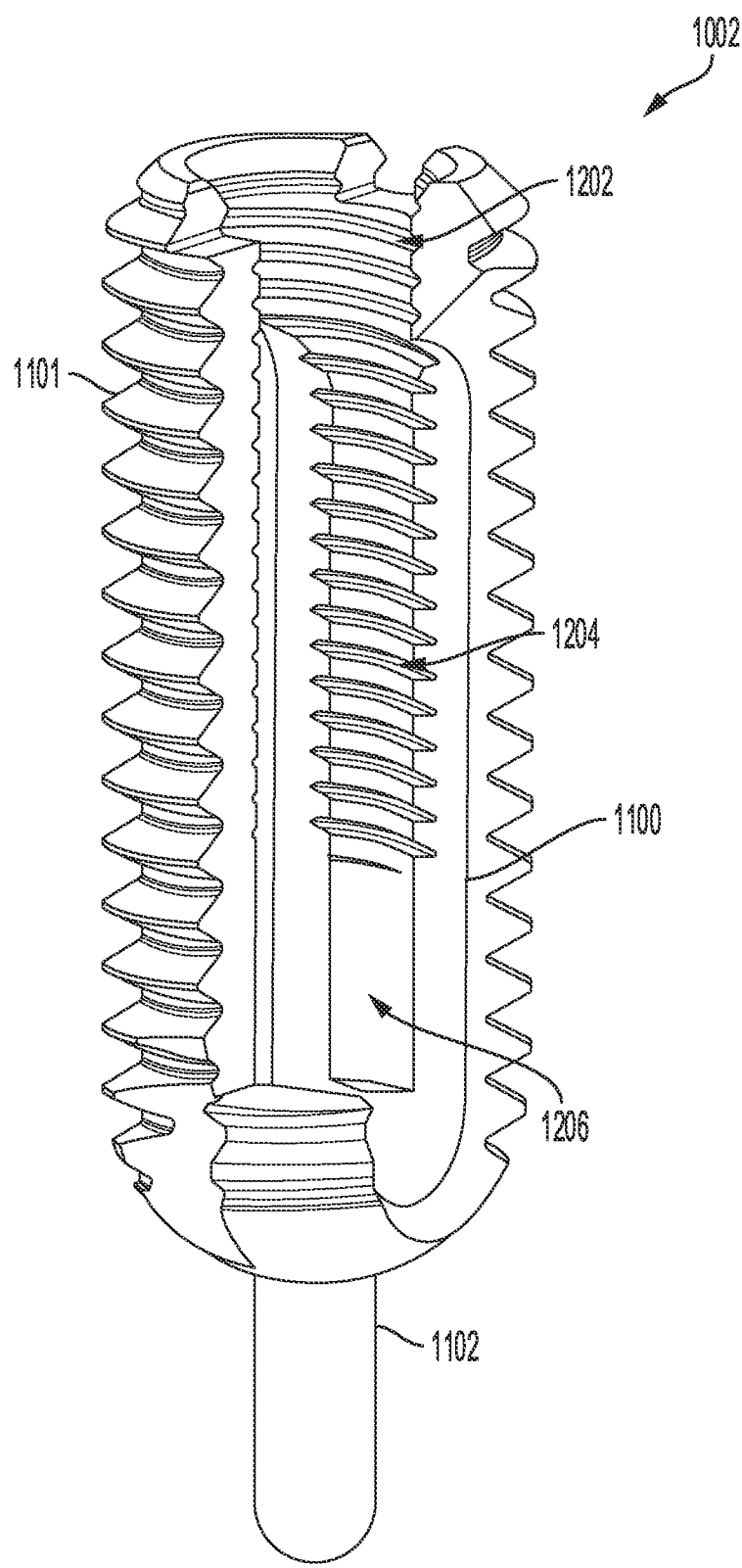
FIG. 12 illustrates a perspective view in partial cross section of the bushing showing the bushing's interior threading, according to an aspect of the present disclosure.

In some examples, the interior of the body portion 1100 may be smooth or otherwise without interior threading. In other examples, the body portion 1100 may include a plurality of interior threads, as illustrated in FIG. 12. In at least some aspects, as shown in FIG. 12, the interior threading of the bushing 1002 may include a portion 1202 of fully formed threads and a portion 1204 of partially formed threads. In some instances, the interior threading may gradually taper from fully formed threads in the portion 1202 to the partially formed threads in the portion 1204. In various instances, the interior of the bushing 1002 includes a portion 1206 having no threading. In some instances, the interior threading may gradually taper from the partially formed threads in the portion 1204 to no threading at all in the portion 1206. The portion 1202, the portion 1204, and the portion 1206 may have any suitable length relative to one another in various aspects.

In some aspects, the interior threading of the busing 1002 may include only partially formed threads. Stated differently, the portion 1204 of partially formed threads may extend the entire length of the interior of the body portion 1100. In some aspects, the interior threading of the bushing 1002 may include only fully formed threads and partially formed threads. For example, the interior of the body portion 1100 may include one or more of the portion 1202 of fully formed threads and one or more of the portion 1204 of partially formed threads. In such examples, the interior of the body portion 1100 may be split into a portion 1202 of fully formed threads and a portion 1204 of partially formed threads, or the fully formed and partially formed sections may alternate (e.g., a portion 1202, a portion 1204, and a portion 1202 along the length of the interior of the body portion 1100). In some aspects, the interior threading of the bushing 1002 may include only one or more portions 1202 of fully formed threads and one or more portions 1206 of no interior threading. In some aspects, the interior threading of the bushing 1002 may include only one or more portions 1204 of partially formed threads and one or more portions 1206 of no interior threading.

Returning to FIG. 11, in at least some aspects, the set screw 1006 includes a plurality of threads 1106. The threads 1106 of the set screw 1006 may be fully formed. In at least some aspects, the set screw 1006 is constructed of a material (e.g., cobalt chromium or stainless steel) that has a greater hardness than the material (e.g., titanium, stainless steel, or a suitable plastic) from which the bushing 1002 is constructed. In at least some examples, as the set screw 1006 having a plurality of threads 1106 that are fully formed is driven or advanced into the bushing 1002, the portion 1204 having partially formed interior threads and the portion 1206 having no threads causes interference with the plurality of threads 1106. This interference causes the plurality of threads 1106 of the set screw 1006 to apply outward force (e.g., in the opposite direction of the arrows 1108A and 1108B) to the side walls of the body portion 1100 of the bushing 1002, pushing the side walls outward. For instance, the set screw 1006 may be constructed of a harder material than the bushing 1002 so that the plurality of threads 1106 of the set screw 1006 pushes into the bushing 1002 rather than vice versa.

Once the set screw 1006 is fully inserted, the set screw 1006 applies compressive force to the nail 1004 in the direction of the arrow 1104, which helps lock the nail 1004 in place. The compressive force creates a tensile force within the bushing 1002 in the direction of the arrow 1104. At the same time, the engagement of the plurality of threads 1106 with the interior threading of the bushing 1002 creates a counter tensile force within the bushing 1002 in the direction of the arrow 1106. The opposing tensile forces in the direction of the arrows 1104 and 1106 attempt to pull the bushing 1002 apart, and also influence the side walls of the body portion 1100 towards one another in the direction of the arrows 1108A and 1108B. The created force in the direction of the arrows 1108A and 1108B counters the outward force applied by the set screw 1006 (e.g., in the opposite direction of the arrows 1108A and 1108B) generated from the interference. The forces countering one another generates friction between the set screw 1006 and the bushing 1002, which prevents the set screw 1006 from loosening. In this way, the bushing 1002 and the set screw 1006 provide a self-locking construct.

Figure 13:
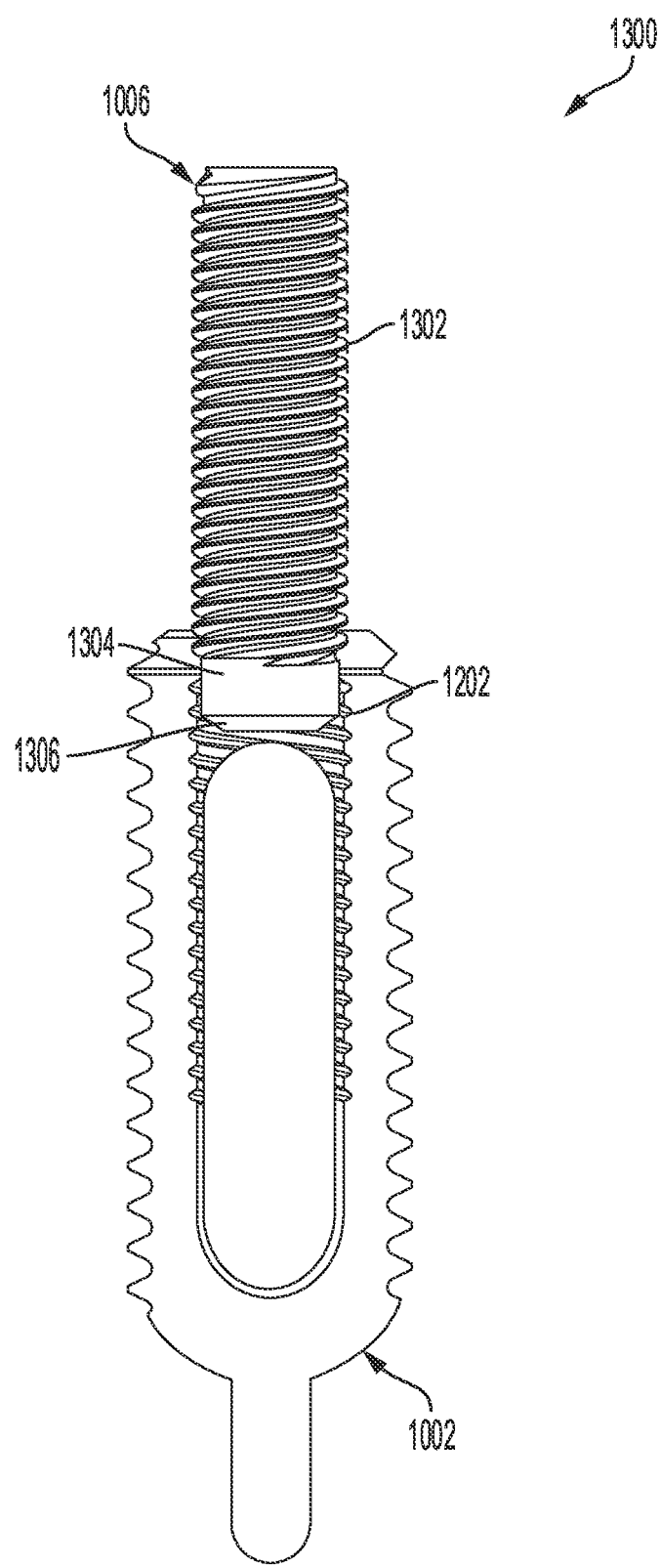
FIG. 13 illustrates a perspective view of a bushing and a set screw having a non-threaded portion and tapered end, according to an aspect of the present disclosure.

In at least some aspects of the present disclosure, the set screw 1006 may include a non-threaded portion 1304 at its leading end, as illustrated in FIG. 13. The non-threaded portion 1304 may be a smooth portion without any exterior threading. In some aspects, the leading end including the non-threaded portion 1304 may be cylindrical. In some aspects, the non-threaded portion 1304 may include a tapered lead end 1306. During a surgical procedure, the set screw 1006 is inserted through a long cannula (e.g., a cannula inserted into the rotary cannula 108) using a long driver, which introduces difficulty in properly guiding the set screw 1006 into the bushing 1002 while avoiding oblique initial insertion and cross-threading. The non-threaded portion 1304, helps to self-orient the set screw 1006 to the bushing 1002 upon insertion. For instance, the non-threaded portion 1304 may be aligned concentrically with the interior threads (e.g., the portion 1202) of the bushing 1002 to help ensure that the set screw 1006 is aligned concentrically with the bushing 1002 prior to engagement of the threads between the set screw 1006 and the bushing 1002. Ensuring that the set screw 1006 and the bushing 1002 are concentrically aligned prior to threaded engagement helps prevent oblique initial insertion of the set screw 1006 and helps prevent cross-threading.

The present disclosure additionally provides a drill component system for preparing a bone for insertion of a fixation component. The fixation component may be, for example, a bushing (e.g., the bushing 1002), a screw or fastener, or another suitable fixation component. In an example, when the bushing 1002 is utilized in a bone fixation procedure, the plurality of exterior threads 1101 on the threaded body portion 1100 engage the bone's near cortex and the nipple 1102 engages the bone's far cortex. In such examples, the provided drill component system may prepare a bone for insertion of a bushing 1002 including such features. In various aspects, the provided drill component system may include a near cortex drill component 1404 (FIGS. 14, 15, and 16) for preparing the near cortex. The provided drill component system may additionally or alternatively include a far cortex drill component (e.g., FIG. 17) for preparing the far cortex. The provided drill component system helps ensure that a surgeon or other medical professional does not accidentally over-drill either the near cortex or the far cortex. Such over-drilling may reduce a fixation component's potential holding power. For example, such over-drilling would reduce the engagement of the bushing 1002 with the bone and would therefore reduce the bushing 1002 and set screw 1006 construct's holding power dramatically. The near cortex drill component and far cortex drill component may each respectively couple to a driving instrument, such as a drill.

Figure 14:
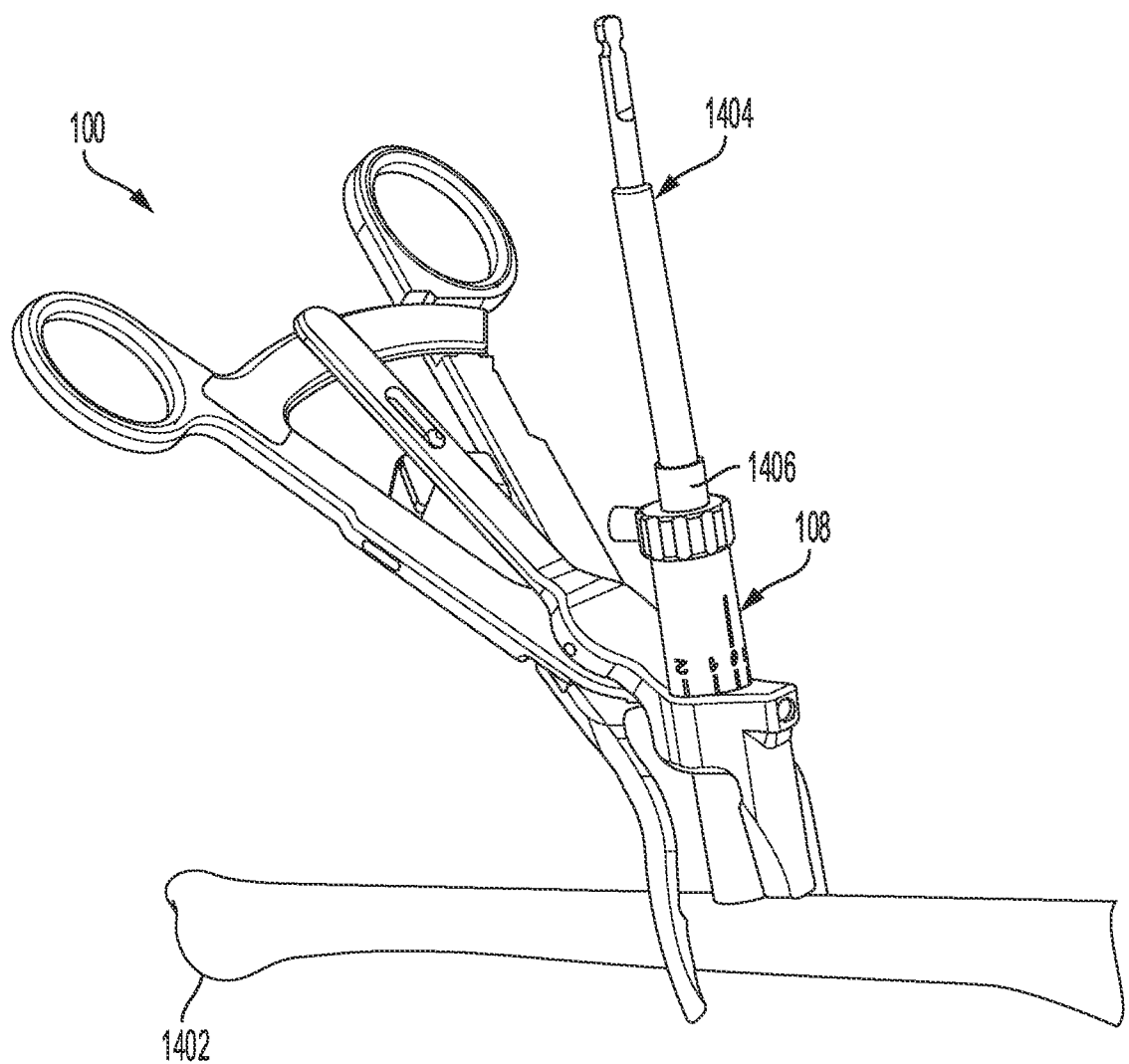
FIG. 14 illustrates a perspective view of a near cortex drill component at a maximum drill depth, according to an aspect of the present disclosure.
Figures 15, 16:
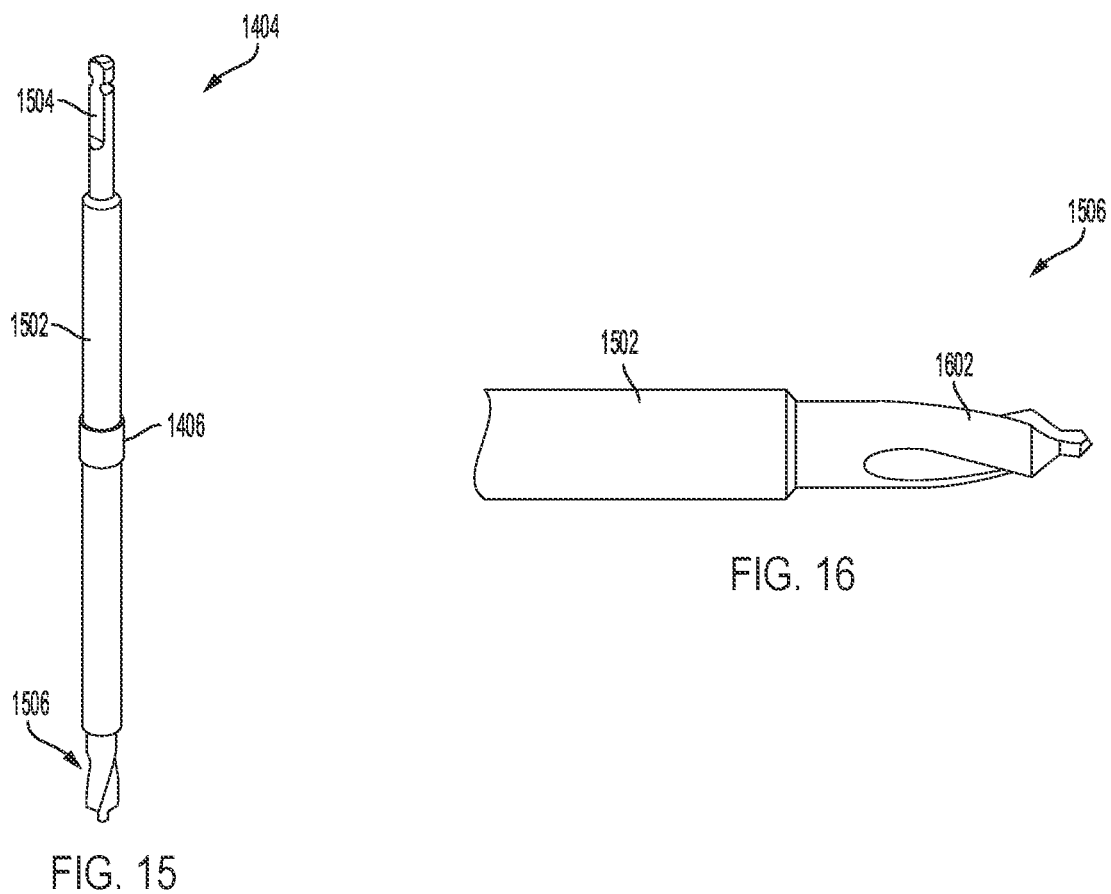
FIG. 15 illustrates a perspective view of a near cortex drill component, according to an aspect of the present disclosure.
FIG. 16 illustrates a magnified perspective view of the near cortex drill component's leading end, according to an aspect of the present disclosure.

FIGS. 14 and 15 illustrate an example near cortex drill component 1404. The near cortex drill component 1404 includes a shaft 1502. A leading end 1506 of the shaft 1502 is configured to cut into bone when driven by a driving instrument. In some aspects, a trailing end 1504 of the shaft 1502 may be configured to couple to a driving instrument. For example, the trailing end 1504 may be configured as an AO connector. In other aspects, the near cortex drill component 1404 may be connected to a driving instrument, rather than being configured to couple to a driving instrument.

In at least some aspects, the shaft 1502 of the near cortex drill component 1404 includes a shoulder 1406. The shoulder 1406 extends outward from the shaft 1502 such that the near cortex drill component 1404 has a greater outer diameter at the shoulder 1406 than at a different location of the shaft 1502. In various aspects, the shoulder 1406 is configured such that when the near cortex drill component 1404 is inserted through a cannula for a surgical procedure, the shoulder 1406 cannot pass through the cannula, thereby limiting the depth to which a surgeon or other medical professional may drill using the near cortex drill component 1404. The shoulder 1406 is particularly positioned on the shaft 1502 to help prevent a surgeon or other medical professional from reaching and drilling into the far cortex with the near cortex drill component 1404. For example, FIG. 14 illustrates the clamp 100 in position for a drilling operation on a bone 1402. The near cortex drill component 1404 is positioned through the rotary cannula 108 at maximum insertion depth with the shoulder 1406 in contact with the rotary cannula 108.

FIG. 16 illustrates a magnified view of the leading end 1506 of the near cortex drill component 1404. In at least some aspects, the leading end 1506 includes a sharp cutting portion 1602 that cuts into bone when the near cortex drill component 1404 is driven by a driving instrument. The sharp cutting portion 1602 is configured such that the bone hole it generates has a diameter smaller than an outer diameter of a fixation component for which the bone hole is prepared. In various aspects, the fixation component may be a bushing (e.g., the bushing 1002), a screw or fastener, or another suitable fixation component. The smaller diameter bone hole than the fixation component's outer diameter enables the fixation component (e.g., its threads) to drive into the bone and effect fixation.

Figure 17:
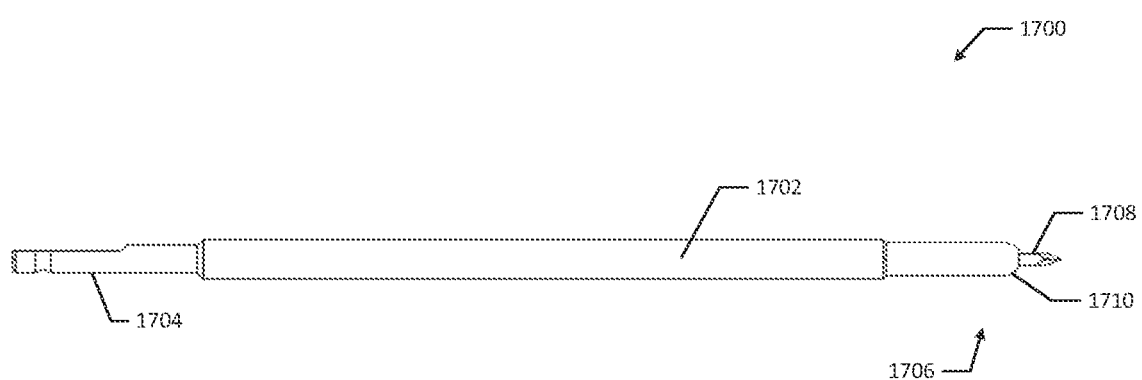
FIG. 17 illustrates a perspective view of a far cortex drill component, according to an aspect of the present disclosure.

FIG. 17 illustrates a side view of an example far cortex drilling component 1700. The far cortex drilling component 1700 includes a shaft 1702. In some aspects, a trailing end 1704 of the shaft 1702 may be configured to couple to a driving instrument. For example, the trailing end 1704 may be configured as an AO connector. In other aspects, the far cortex drill component 1700 may be connected to a driving instrument, rather than being configured to couple to a driving instrument. The leading end 1706 of the far cortex drilling component 1700 is configured to cut into bone when the far cortex drilling component 1700 is driven by a driving instrument. In at least some instances, a surgeon or other medical professional may utilize the far cortex drilling component 1700 after drilling a hole into the near cortex of the bone using the near cortex drilling component 1404.

In at least some aspects, the leading end 1706 of the far cortex drilling component 1700 includes a blunt reamer portion 1710. A sharp trocar tip 1708 may extend from the blunt reamer portion 1710. The blunt reamer portion 1710 may have a larger diameter than the sharp trocar tip. As a surgeon or other medical professional drives the far cortex drilling component 1700 into a bone, the sharp trocar tip 1708 may generate a hole in the far cortex. The generated hole in the far cortex has a smaller diameter than the hole the near cortex drilling component 1404 generated in the bone. In at least some aspects, the blunt reamer portion 1710 is configured such that it does not penetrate or advance into bone. In such aspects, the blunt reamer portion 1710 both prevents the shaft 1702 of the far cortex drill component 1700 from penetrating the far cortex and limits the depth to which the sharp trocar tip 1708 may advance into or through the far cortex, since the sharp trocar tip 1708 has a definite length and can advance no further than the definite length.

In at least some aspects, the sharp trocar tip 1708 is constructed such that the hole it generates corresponds to at least a portion of a fixation component used for a procedure. For example, the hole may correspond to a diameter of a screw. In another example, the sharp trocar tip 1708 may be constructed such that the hole it generates in the far cortex corresponds to the nipple 1102 of the bushing 1002. In such examples, the hole generated by the sharp trocar tip 1708 may therefore provide a conforming fit for the nipple 1102 so that bushing 1002 maintains its position or fixation in the bone once installed. In at least some aspects, the blunt reamer portion 1710 may be constructed with a shape such that it contours the inside of the bone canal to correspond to the shape of at least a portion of a fixation component used for the procedure. For example, the blunt reamer portion 1710 may contour the inside of the bone canal to correspond to the body portion 1100 of the bushing 1002. In such examples, once the bone canal is contoured by the blunt reamer portion 1710, the plurality of exterior threads 1101 on the bushing 1002 may evenly advance into the bone wall to help provide maximum engagement of the plurality of exterior threads 1101 and stability of the bushing 1002.

An example method for preparing a bone for nail-based fixation is also provided. A surgeon may select at least one fixation component (e.g., the bushing 1002) having a particular size. The surgeon may then select a first drill component (e.g., the near cortex drill component 1404) corresponding to the selected size of the bushing 1002. A second drill component (e.g., the far cortex drill component 1700) may also be selected corresponding to the selected size of the bushing 1002. The surgeon may insert the near cortex drill component 1404 through a cannula (e.g., the rotary cannula 108 of the clamp 100) that is in contact with a bone. The near cortex drill component 1404 may be coupled or connected to a powered drilling instrument. With the near cortex drill component 1404 inserted through the rotary cannula 108, the surgeon may drill through a near cortex of the bone to form a bone hole in the near cortex. The near cortex drill component 1404 may then be removed from the rotary cannula 108.

The surgeon may subsequently insert the far cortex drill component 1700 through the rotary cannula 108. The far cortex drill component 1700 may be coupled or connected to a powered drilling instrument. With the far cortex drill component 1700 inserted through the rotary cannula 108, the surgeon may drill through the bone hole generated by the near cortex drill component 1404 and into a far cortex of the bone thereby forming a second bone hole in the far cortex. The far cortex drill component 1700 may then be removed from the rotary cannula 108. With the bone holes prepared in the near cortex and the far cortex, the surgeon may install the bushing 1002 in the prepared bone holes. In at least some aspects of this example, the surgeon may install a nail (e.g., the nail 1004) through an opening (e.g., the opening 1110) of the bushing 1002. With the nail 1004 installed through the opening 1110, the surgeon may install a set screw (e.g., the set screw 1006) in the bushing 1002 such that the set screw 1006 locks the nail 1004 to the bushing 1002.

The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A clamp device for use in a bone fixation procedure comprising:
   a first arm including a handle at one end opposite a clamping end, and a first elongated slot in between the two ends of the first arm, the first elongated slot extends through the first arm in a direction of elongation and opens toward the clamping end of the first arm;
   a second arm including a handle at one end opposite a clamping end, and a second elongated slot in between the two ends of the second arm, the second elongated slot extends through the second arm in a direction of elongation and opens toward the clamping end of the second arm;
   a cannula block including a body portion having a channel extending through the body portion, a post extending from the body portion, and a cap at an end of the post; and
   a rotary cannula including a body portion having a cannulation along the body portion's long axis, wherein the rotary cannula is configured to be positioned through the channel of the cannula block,
   wherein each of the first arm, the second arm, the cannula block, and the rotary cannula are distinct, separate components that are configured to allow the clamp device to be repeatedly assembled and disassembled into the clamp device's distinct, separate components,
   wherein in an operate configuration, the post of the cannula block is positioned within the first and second elongated slots, which allows the first and second arms to rotate about the post to move the clamping ends away from and towards each other to clamp a bone to maintain a position of the clamp device relative to the bone,
   wherein the body portion of the cannula block includes a tab within the channel, wherein the body portion of the rotary cannula includes a flat surface and a groove extending around the rotary cannula' s body portion and terminating at the flat surface, and wherein the tab is configured to translate within the groove when rotating the rotary cannula within the cannula block,
   wherein the cannula block and the rotary cannula are configured to allow the rotary cannula to only be axially translated through the channel of the cannula block when the tab is oriented with the flat surface, and
   wherein the cannula block and the rotary cannula are configured such that the rotary cannula is locked to the cannula block, such that the rotary cannula is prevented from translating along the long axis of the rotary cannula' s body portion, upon rotating the rotary cannula so that the tab is positioned within the groove.

2. The clamp device of claim 1, wherein the first arm, the second arm, and the cannula block are configured such that the first and second arms prevent the post of the cannula block from exiting the first and second elongated slots in the operate configuration.

3. The clamp device of claim 1, wherein the first arm, the second arm, and the cannula block are configured such that disassembling the clamp device includes manipulating the first and second arms to line up the first elongated slot with the second elongated slot and enable the post of the cannula block to translate out of the first and second elongated slots.

4. The clamp device of claim 1, wherein the cap is configured such that, in an assembled configuration, the cap prevents the first arm or the second arm from translating in an axial direction of the post.

5. The clamp device of claim 1, wherein the first arm and the second arm are connected such that the connection limits an opening of the first and second arms.

6. The clamp device of claim 5, wherein the first and second arms are connected by a ratcheted connection including a ratchet member and a ratchet receiver.

7. The clamp device of claim 1, wherein a length of the post is approximately equal to a sum of a first thickness of the first arm at the first elongated slot and a second thickness of the second arm at the second elongated slot.

8. The clamp device of claim 1, wherein the first or second arm includes a branch having a rod and the other of the first or second arm includes a branch having an opening configured such that the rod conformingly fits through the opening.

9. The clamp device of claim 8, wherein the cannula block includes an elongated opening configured such that the rod is positioned within the elongated opening in an assembled configuration.

10. The clamp device of claim 1, wherein the cannula block includes a plurality of fixation instrument openings.

11. The clamp device of claim 1, further comprising a scale of indicators or numerals corresponding to a distance between the respective clamping ends of the first and second arms.

12. The clamp device of claim 1, further comprising a scale of indicators or numerals corresponding to an amount of compressive force applied between the respective clamping ends of the first and second arms.

13. A clamp device for use in a bone fixation procedure comprising:
- a first arm and a second arm configured to rotate with respect to one another about a shared axis, each of the first and second arms includes a handle at one end opposite a clamping end, and an elongated slot in between the ends such that a first elongated slot extends through the first arm in a direction of elongation and opens toward the clamping end of the first arm, and a second elongated slot extends through the second arm in a direction of elongation and opens toward the clamping end of the second arm;
- a cannula block including a body portion having a post extending from the body portion and terminating in a cap, a channel extending through the body portion, and a tab that extends within the channel; and
- a rotary cannula including a body portion having a cannulation along the body portion's long axis, wherein the body portion of the rotary cannula further includes a flat surface and a groove extending around the rotary cannula's body portion and terminating at the flat surface, wherein the groove is configured to allow the rotary cannula to be rotated within the channel of the cannula block with the tab positioned within the groove,
- wherein the cannula block and the rotary cannula are configured to allow the rotary cannula to only be axially translated through the channel of the cannula block when the tab is oriented with the flat surface, and
- wherein rotating the rotary cannula such that the tab is positioned within the groove locks the rotary cannula to the cannula block such that the rotary cannula is prevented from translating along the long axis of the rotary cannula's body portion,
- wherein each of the first arm, the second arm, the cannula block, and the rotary cannula are distinct, separate components that are configured to allow the clamp device to be repeatedly assembled and disassembled into the clamp device's distinct, separate components, and
- wherein in an operate configuration, the post of the cannula block is positioned within the elongated slots of the first and second arms, which allows the first and second arms to rotate about the post, defining the shared axis, to move the clamping ends away from and towards each other to clamp a bone to maintain a position of the clamp device relative to the bone.

14. The clamp device of claim 13, wherein the cannula block and the rotary cannula are configured such that the channel of the cannula block and the cannulation of the rotary cannula are not coaxial when the rotary cannula is positioned within the cannula block.

15. The clamp device of claim 14, wherein the cannula block further includes a plunger configured to extend into the channel in a relaxed state and configured to be compressed into the cannula block's body portion upon applied force to the plunger.

16. The clamp device of claim 15, wherein the body portion of the rotary cannula includes a plurality of detents configured to accept a tip of the plunger.

17. The clamp device of claim 16, wherein at least a portion of the detents are positioned on the body portion of the rotary cannula such that they each correspond to a discrete offset amount of a long axis of the cannulation of the rotary cannula relative to a long axis of the channel of the cannula block.

* * * * *